(12) United States Patent
Davis et al.

(10) Patent No.: US 7,803,838 B2
(45) Date of Patent: Sep. 28, 2010

(54) COMPOSITIONS COMPRISING NEBIVOLOL

(75) Inventors: Eric Davis, Morgantown, WV (US); John O'Donnell, Morgantown, WV (US); Peter Bottini, Morgantown, WV (US)

(73) Assignee: Forest Laboratories Holdings Limited (BM)

( * ) Notice: Subject to any disclaimer, the term of this patent is extended or adjusted under 35 U.S.C. 154(b) by 455 days.

(21) Appl. No.: 11/141,235

(22) Filed: May 31, 2005

(65) Prior Publication Data

US 2005/0272810 A1    Dec. 8, 2005

Related U.S. Application Data

(60) Provisional application No. 60/577,423, filed on Jun. 4, 2004.

(51) Int. Cl.
*A61K 31/352* (2006.01)
*C07D 311/04* (2006.01)

(52) U.S. Cl. .......................... 514/456; 514/1; 514/451

(58) Field of Classification Search .................. 514/1, 514/183, 451, 456
See application file for complete search history.

(56) References Cited

U.S. PATENT DOCUMENTS

| | | | |
|---|---|---|---|
| 5,874,461 A | 2/1999 | De Chaffoy de Courcelles et al. | |
| 5,922,341 A | 7/1999 | Smith et al. | |
| 6,075,046 A | 6/2000 | De Chaffoy de Courcelles et al. | |
| 6,465,463 B1 | 10/2002 | Cohn et al. | |
| 6,495,154 B1 | 12/2002 | Tam et al. | |
| 6,541,479 B1 | 4/2003 | Mehanna et al. | |
| 6,545,040 B1 | 4/2003 | Xhonneux et al. | |
| 6,595,926 B1 | 7/2003 | Laragh | |
| 6,596,744 B2 | 7/2003 | Wagle et al. | |
| 6,596,745 B2 | 7/2003 | Gall | |
| 6,632,180 B1 | 10/2003 | Laragh | |
| 6,635,273 B1 | 10/2003 | Loscalzo et al. | |
| 6,770,663 B2 | 8/2004 | Wagle et al. | |
| 6,784,177 B2 | 8/2004 | Cohn et al. | |
| 6,869,966 B2 | 3/2005 | Sato et al. | |
| 6,946,141 B2 | 9/2005 | Tam et al. | |
| 6,951,860 B2 | 10/2005 | Mehanna et al. | |
| 7,030,106 B2 | 4/2006 | Cho | |
| 7,056,906 B2 | 6/2006 | Strony | |
| 2001/0008896 A1 | 7/2001 | Smith et al. | |
| 2001/0044584 A1 | 11/2001 | Kensey | |
| 2002/0032149 A1 | 3/2002 | Kensey | |
| 2002/0061835 A1 | 5/2002 | Kensey | |
| 2002/0068729 A1 | 6/2002 | Egan et al. | |
| 2002/0107245 A1 | 8/2002 | Wagle et al. | |
| 2002/0115655 A1 | 8/2002 | Mehanna et al. | |
| 2002/0123485 A1 | 9/2002 | Alexander et al. | |
| 2002/0147184 A1 | 10/2002 | Kosoglou et al. | |
| 2002/0151536 A1 | 10/2002 | Davis et al. | |
| 2002/0161016 A1 | 10/2002 | Tam et al. | |
| 2002/0169134 A1 | 11/2002 | Davis | |
| 2002/0177586 A1 | 11/2002 | Egan et al. | |
| 2002/0183305 A1 | 12/2002 | Davis et al. | |
| 2002/0183317 A1 | 12/2002 | Wagle et al. | |
| 2002/0183365 A1 | 12/2002 | Wagle et al. | |
| 2002/0192203 A1 | 12/2002 | Cho | |
| 2003/0004194 A1 | 1/2003 | Gall | |
| 2003/0013699 A1 | 1/2003 | Davis et al. | |
| 2003/0027820 A1 | 2/2003 | Gall | |
| 2003/0053981 A1 | 3/2003 | Davis et al. | |
| 2003/0060489 A1 | 3/2003 | Buckingham | |
| 2003/0069221 A1 | 4/2003 | Kosoglou et al. | |
| 2003/0078190 A1* | 4/2003 | Weinberg ...................... 514/1 |
| 2003/0078517 A1 | 4/2003 | Kensey | |
| 2003/0119428 A1 | 6/2003 | Davis et al. | |
| 2003/0119757 A1 | 6/2003 | Davis | |
| 2003/0119796 A1 | 6/2003 | Strony | |
| 2003/0119808 A1 | 6/2003 | LeBeaut et al. | |
| 2003/0119809 A1 | 6/2003 | Davis | |
| 2003/0162824 A1 | 8/2003 | Krul | |
| 2003/0175344 A1 | 9/2003 | Wald et al. | |
| 2003/0176426 A1 | 9/2003 | Wagle et al. | |
| 2003/0225146 A1 | 12/2003 | Wagle et al. | |
| 2004/0005306 A1 | 1/2004 | Loscalzo et al. | |
| 2004/0023967 A1 | 2/2004 | Cohn et al. | |
| 2004/0054177 A1 | 3/2004 | Otake et al. | |
| 2004/0063646 A1 | 4/2004 | Fujikura et al. | |

(Continued)

FOREIGN PATENT DOCUMENTS

EP    1 400 529    3/2004

(Continued)

OTHER PUBLICATIONS

Neutel J., "Clinical Studies of CS-866, the Newest Angiotensin II Receptor Antagonist." American Journal of Cardiology 2001: 87(suppl);37c-43c.*

(Continued)

*Primary Examiner*—Frederick Krass
*Assistant Examiner*—Walter E Webb
(74) *Attorney, Agent, or Firm*—Charles Ryan, J.D.; Michael Cirado, J.D.

(57) ABSTRACT

Nebivolol has been shown to be beneficial in the treatment of cardiovascular diseases such hypertension, congestive heart failure, arterial stiffness and endothelial dysfunction. The present invention features a pharmaceutical composition comprising nebivolol and at least one other active agent, wherein the at least one other active agent is a cardiovascular agent.

12 Claims, 4 Drawing Sheets

U.S. PATENT DOCUMENTS

| | | |
|---|---|---|
| 2004/0071766 A1 | 4/2004 | Loscalzo et al. |
| 2004/0071777 A1 | 4/2004 | Trespidi et al. |
| 2004/0097482 A1 | 5/2004 | Davis et al. |
| 2004/0097495 A1 | 5/2004 | Wagle et al. |
| 2004/0105850 A1 | 6/2004 | Loscalzo et al. |
| 2004/0109894 A1 | 6/2004 | Shefer et al. |
| 2004/0132805 A1 | 7/2004 | Garvey |
| 2004/0176308 A1 | 9/2004 | Shiohara et al. |
| 2004/0176373 A1 | 9/2004 | Buckingham |
| 2004/0180860 A1 | 9/2004 | Burnett et al. |
| 2004/0180861 A1 | 9/2004 | Burnett et al. |
| 2004/0197482 A1 | 10/2004 | Lamaze et al. |
| 2004/0198700 A1 | 10/2004 | Burnett et al. |
| 2004/0214811 A1 | 10/2004 | Davis et al. |
| 2004/0235809 A1 | 11/2004 | Alexander et al. |
| 2004/0235837 A1 | 11/2004 | Egan et al. |
| 2005/0014747 A1 | 1/2005 | Reinhard et al. |
| 2005/0031651 A1 | 2/2005 | Gervais et al. |
| 2005/0032788 A1 | 2/2005 | Wagle et al. |
| 2005/0032879 A1 | 2/2005 | Okarter et al. |
| 2005/0074487 A1 | 4/2005 | Hsu et al. |
| 2005/0080071 A1 | 4/2005 | Davis |
| 2005/0096307 A1 | 5/2005 | Graziano |
| 2005/0153952 A1 | 7/2005 | Cho |
| 2005/0215537 A1 | 9/2005 | Alexander et al. |
| 2005/0222161 A1 | 10/2005 | Moriya et al. |
| 2005/0239766 A1 | 10/2005 | Starke et al. |
| 2005/0272669 A1 | 12/2005 | Fushimi et al. |
| 2005/0272763 A1 | 12/2005 | Toupence et al. |
| 2005/0272810 A1 | 12/2005 | Davis et al. |
| 2006/0009399 A1 | 1/2006 | Davis et al. |
| 2006/0009513 A1 | 1/2006 | Garvey |
| 2006/0014828 A1 | 1/2006 | Worcel et al. |
| 2006/0014829 A1 | 1/2006 | Worcel et al. |
| 2006/0024238 A1 | 2/2006 | Barth et al. |
| 2006/0025352 A1 | 2/2006 | Fujikura et al. |
| 2006/0069080 A1 | 3/2006 | Veltri |
| 2006/0089349 A1 | 4/2006 | Gundertofte et al. |
| 2006/0094699 A1 | 5/2006 | Kampen et al. |
| 2006/0100235 A1 | 5/2006 | Andersen et al. |
| 2006/0106008 A1 | 5/2006 | Andersen et al. |
| 2006/0106046 A1 | 5/2006 | Moriya et al. |
| 2006/0110444 A1 | 5/2006 | Holm et al. |
| 2006/0111348 A1 | 5/2006 | Kampen et al. |
| 2006/0111366 A1 | 5/2006 | Andersen et al. |
| 2006/0111380 A1 | 5/2006 | Otake et al. |
| 2006/0142209 A1 | 6/2006 | Nishimura et al. |
| 2006/0142288 A1 | 6/2006 | Peroutka |
| 2006/0148721 A1 | 7/2006 | Erondu |

FOREIGN PATENT DOCUMENTS

| | | |
|---|---|---|
| EP | 1 405 859 | 4/2004 |
| EP | 1 541 175 | 6/2005 |
| EP | 1 544 208 | 6/2005 |
| EP | 1 548 024 | 6/2005 |
| EP | 1 550 668 | 7/2005 |
| EP | 1 553 091 | 7/2005 |
| EP | 1 637 539 | 3/2006 |
| WO | WO 97/49394 | 12/1997 |
| WO | WO 00/38653 | 7/2000 |
| WO | WO 01/12584 | 2/2001 |
| WO | WO 01/17528 | 3/2001 |
| WO | WO 01/35961 | 5/2001 |
| WO | WO 01/47509 | 7/2001 |
| WO | WO 01/76632 | 10/2001 |
| WO | WO 01/97832 | 12/2001 |
| WO | WO 02/05851 | 1/2002 |
| WO | WO 02/07725 | 1/2002 |
| WO | WO 02/09760 | 2/2002 |
| WO | WO 02/34303 | 5/2002 |
| WO | WO 02/41883 | 5/2002 |
| WO | WO 02/43806 | 6/2002 |
| WO | WO 02/053161 | 7/2002 |
| WO | WO 02/058685 | 8/2002 |
| WO | WO 02/058731 | 8/2002 |
| WO | WO 02/058733 | 8/2002 |
| WO | WO02058731 | 8/2002 |
| WO | WO 02/067851 | 9/2002 |
| WO | WO 02/058732 | 10/2002 |
| WO | WO 02/087508 | 11/2002 |
| WO | WO 02/096362 | 12/2002 |
| WO | WO 02/096363 | 12/2002 |
| WO | WO 02/096415 | 12/2002 |
| WO | WO 03/024456 | 3/2003 |
| WO | WO 03/026643 | 4/2003 |
| WO | WO 03/026644 | 4/2003 |
| WO | WO 03/068186 | 8/2003 |
| WO | WO 03/092617 | 11/2003 |
| WO | WO03092617 | 11/2003 |
| WO | WO 2004/024720 | 3/2004 |
| WO | WO 2004/031175 | 4/2004 |
| WO | WO 2004/047837 | 6/2004 |
| WO | WO2004089416 | 10/2004 |
| WO | WO2004110375 | 12/2004 |
| WO | WO2005000217 | 1/2005 |
| WO | WO 2005/046797 | 5/2005 |
| WO | WO 2005/047285 | 5/2005 |
| WO | WO 2005/065639 | 7/2005 |
| WO | WO 2005/099699 | 10/2005 |
| WO | WO2005099699 | 10/2005 |
| WO | WO 2005/102304 | 11/2005 |
| WO | WO 2005/107384 | 11/2005 |
| WO | WO 2005/117591 | 12/2005 |
| WO | WO 2005/117858 | 12/2005 |
| WO | WO2005113012 | 12/2005 |
| WO | WO 2006/012642 | 2/2006 |
| WO | WO 2006/015830 | 2/2006 |
| WO | WO 2006/020244 | 2/2006 |
| WO | WO 2006/025070 | 3/2006 |
| WO | WO2006069293 | 6/2006 |

OTHER PUBLICATIONS

Maas et al., "Antihypertensive therapy: special focus on drug interactions." Expert Opin. Drug Saf. 2003:2(6);549-579.*

Cruickshank, J.M., "Beta-blockers and diabetes: the bad guys come good", Cardiovascular Drugs and Therapy, vol. 16, No. 5, pp. 457-470, 2002.

Whitworth, J.A.,, "Emerging drugs in the management of hypertension", Expert Opinion on Emerging Drugs, vol. 8, No. 2, pp. 377-388, 2003.

Kolck, et al., "Pharmacological basis of antihypertension drug therapy", vol. 93, No. 20, pp. 847-856, May 12, 2004.

"Rationale for Fixed-Dose Combinations in the Treatment of Hypertension", Drugs, 2002, D.A. Sica, vol. 62 (3), pp. 443-462.

"Hypertension Primer, Third Edition" Izzo and Black, 2003 pp. 408-429 (Chapter C138).

Kamali, F., at al; A pharmacokinetic and pharmacodynamic interaction study between nebivolol . . . ; 1977 Blackwell Science Ltd Br / Clin Pharmacol ; 43; pp. 201-204.

Nebivolol; Drugs of the Future, vol. 14; No. 10; 1989; pp. 957-959.

Lu, H.R., et al.; Effectsof B-adrenoceptor antagoinists on cardiac function in ischemic-reperfused . . . ; European Journal of Pharmacology, 184 (1990) 65-74.

Sieben, G., et al.; Nebivolol in Hypertension . . . ; First Intern'l Nebivolol Investigators' Mtg, Antwerp, Belgium; Sep. 13-15, 1990; Drug Investigation 3 (suppl. 1) pp. 193-195.

XI Journees de I'Hypertension Arterielle de la Societe Francaise de Cardiologie; Paris, France, Dec. 12-13, 1991; Archives des Maladies du coeur et des vaisseaux 84 p. 50.

Nebivolol; Phase III Profiles 2 (7); (Jul. 1992) pp. 10-14.

Eighth Scientific Meeting of the American Society of Hypertension, New York, New York, USA (May 19-22, 1993); American Journal of Hypertension 6 (5, part 2) p. 100A.
Ford, G.A.; Endothelial Dependcent Venodilatory Action Of Nebivolol In Human Hand Veins; 6th European Meeting on Hypertension, Milan, Italy, Jun. 4-7, 1993; pp. 239-240.
Lafabvre, J., et al.; Formule De Resume; (Oct. 20, 1993); 1 pg.
Bortel, L. M. A. B. V.; Beyond The Tension Of Hypertension focus on non-antihypertensive aspects of anihypertensive treatment (Nov. 18, 1993).
Lacourciere, Yves, et al.; Placebo-controlled comparison of the effects of nebivolol . . . ; Journal of Human Hypertension (1994) 8, pp. 283-288.
Lacourciere, Yves, et al., Treatment of Ambulatory Hypertensives with Nebivolol . . . ; American Journal of Hypertension, Ltd. (Feb. 1994) 7:137-145.
15th Scientific Meeting of the ISOH, Melbourne, Australia (Mar. 20-24, 1994); Journal of Hypertension 12 (Suppl. 3) p. 12.
15th Scientific Meeting of the ISOH, Melbourne, Australia (Mar. 20-24, 1994); Journal of Hypertension 12 (Suppl. 3) p. 70.
Kamali, F., et al.; The effects of ranitidine and cimetidine on the . . . ; Proceed of the BPS, Oxford, UK, Jul. 12-14, 1995; British Journal Clinical Pharmac 40; pp. 519P-520P.
Janssens W.J., et al.; Symposium on: Endothelium in Hypertension. New Therapeutic Trends, Berlin, Germany (Mar. 1, 1997) p. 10-13.
Cases, A.; Clinical Pharmacology of Nebivolol; Drugs of Today 1999, 35 (9); pp. 685-699.
McNeely, W. et al.; Nebivolol in the Management of Essential Hypertension A Review; Adis Drug Evaluation; Drugs (Apr. 1999) 57 (4); pp. 633-651.
Schachter M.; Nevivolol: how different, how interesting?; British Journal of Cardiology 7 (6), pp. 341, 343, 345, 347 (2000).
Nitric Oxide: Biology and Chemistry Abstracts; vol. 4, No. 3; pp. 177-323 (2000); Academic Press Nebivolol: a possible novel mechanism in hypertension?; Drugs & Therapy Perspe.
Gosgnach, W., et al.; Nebivolol Induces Calcium-Independent Signaling in Endothelial . . . ; Journal of Cardiovascular Pharmacology, vol. 38, No. 2, 2001; pp. 191-199.
10th International Congress on Cardiovascular Pharmacotherapy, Kyoto, Japan (Mar. 27-31, 2001); Cardiovascular Drugs and Therapy 15 (Suppl. 1) p. 112.
Tzemos, Nikolaos, et al.; Nebivolol Reverses Endothelial Dysfunction in Essential Hypertension; Brief Rapid Communication (Jun. 8, 2001); pp. 511-514.
Yakushin, S.S., et al.; Assessment of the Safety and Antihypertensive Effectiveness of the Cardioselective Beta-Adrenoblocker Nebivolol in . . . ; Kardiologiia 2002, 11:36-39.
Zadionchenko, V.S., et al.; Effects of Nevibolol on Microcirculation, Platelet Aggregation and Blood Viscosity in . . . ; Kardiologiia 2002; 5:14-18.
Amudha, K., et al.; Ethnicity and Drug Therapy for Hypertension; Current Pharmaceutical Design, 2003, 9; pp. 1691-1701; 2003 Bentham Science Publishers Ltd.
Rosei, E.A., et al.; Evaluation of the Efficacy and Tolerability of Nebivolol versus Lisinopril in the Treatment of Essential . . . ; Blood Pressure 2003; 12 (Suppl. 1); 30-35.
Rizos, E., et al.; The Combination of nebivolol plus . . . ; Journal of Cardiovascular Pharmacology and Therapeutics, Jun. 2003 v8 i2 p. 127(8); Westminster Publications Inc.
Cockcroft, J., "Nebivolol: a review," Expert Opinion of Pharmacology, vol. 5(4) (Jan. 1, 2004) pp. 893-899.
European Search Report dated Jul. 28, 2008 for Application No. EP 08 00 6021.
Bruntun, T. Lauder, "Use of Nitrate of Amyl in Angina Pectoris", London Hospital Medicine and Surgery, Jul. 1867, 97-98.
Vanhoutte, "Inhibition by Acetylcholine of Adrenergic neurotransmission in Vascular Smooth Muscle", Circ. Res. 1974;34:317-326.
Kamal, F., et al; "A pharmacokinetic and pharmocodynamic interaction study between nebivolol and the H2-receptor antagonists cimetidine and ranitdine"; 1977 Blackwell Science Ltd Br J. Clin Pharmacol ; 43; pp. 201-204.

Gruetter, et al., "Relaxation of Bovine Coronary Artery and Activation of Coronary Arterial Guanylate Cyclase by Nitric Oxide, Nitroprusside and A Carcinogenic nitrosoamine", Journal of Cyclic Nucleotide Research, 5(3)211-224, 1979.
Furchgott et al., "The obligatory role of endothelial cells in the relaxation of arterial smooth muscle by acetylcholine", Nature vol. 288, Nov. 27, 1980.
Gryglewski, et al., Superoxide anion is involved in the breakdown of endothelium-derived vascular relaxing factor, Letters to Nature, vol. 320, No. 3, Apr. 1986.
Parthasarathy, et al., "Probucol Inhibits Oxidative Modification of Low Density Lipoprotein", The American Society for Clinical Investigation, vol. 77, Feb. 1986.
Harrison et al., "Alterations of Vascular Reactivity in Atherosclerosis", Circulation Research 1987; 61 (suppl II):II-74-II-80.
Palmer, et al., "Nitric oxide release accounts for the biological activity of endothelium-derived relaxing factor", Letters to Nature, vol. 327, Jun. 1987.
Andrews, et al., "Low-density lipoproteins inhibit endothelium-dependent relaxation in rabbit aorta", vol. 327, May 1987.
Bossaller, et al., "Impaired Muscarinic Endothelium-dependent Relaxation and Cyclic Guanosine 5'-Monophosphate Formation in Atherosclerotic Human Coronary Artery and Rabbit Aorta", The American Society for Clinical Investigation, vol. 79, 170-174, 1987.
Van Bortel and Rahn "Effect of nebivolol on the response of isoprenaline in man" International symposium on cardiovascular disease and B-adrenoceptor function Oct. 8 p. 54-65, 1988.
De Cree, et al. "An open pilot study on the effects of nebivolol in 5 patients with acute congestive heart failure"; International Symposium on Cardiovascular Disease and B-adrenoceptor function, Oct. 8 pp. 54-55, 1988.
Pauwels, et al., "The Receptor Binding Profile of the New Antihypertensive Agent Nebivolol and Its Stereoisomers Compared with Various β-Adrenergis Blockers", Janssen Research Foundation, Dept. of Biochemical Pharmacology, B-2340 Beerse, Belgium, Aug. 23, 1988.
Pauwels, et al., "β-Adrenoceptor-mediated cAMP accumulation in cardiac cells: effects of nebivolol", European Journal of Pharmacology-Molecular Pharmacology Section 172 (1989) 417-479.
"Nebivolol; Drugs of the Future," vol. 14; No. 10; 1989; pp. 957-959.
Panza, et al. "Abnormal Endothelium-dependent vascular relaxation in patients with essential hypertension", N Engl J Med., 1990: 323-22-7.
Lu, Hr., et al. "Effects of B-adrenoceptor antagoinists on cardiac function in schemic-reperfused myocardium of the isolated working rabbit heart"; European Journal of Pharmacology, 184 (1990) 65-74.
Sieben, G., et al.; "Nebivolol in Hypertension . . . ;" First Intern'l Nebivolol Investigators' Mtg, Antwerp, Belgium; Sep. 13-15, 1990; Drug Investigation 3 (suppl. 1) pp. 193-195.
Xhonneux et al., "The I-enantiomer of nebivolol potentiates the blood pressure lowering effect of the d-enantiomer", European Journal of Pharmacology 1990, 181:261-265.
Gao, et al., "Nebivolol induces endothelium-dependent relaxations of canine coronary arteries", Journal of Cardiovascular Pharmacology, 1991, 17:964-969.
XI Journees de l'Hypertension Arterielle de la Societe Francaise de Cardiologie; Paris, France, Dec. 12-13, 1991; Archives des Maladies du coeur et des vaisseaux 84 p. 50.
Shimokawa, et al., Loss of Endothelial Pertussis Toxin-Sensitive G Protein Function in Atherosclerotic Porcine Coronary Arteries, Circulation, 83:652-660, 1991.
Drexler et al., "Correction of Endothelial Dysfunction in Coronary Microcirculation of Hypercholesterolaemic Patients by L-Arginine", Lancet, 338: 1546-1550, 1991.
Nebivolol; Phase III Profiles Journal 2 (7); (Jul. 1992) pp. 10-14.
Creager, et al., "$_L$-Arginine Improves Endothelium-dependent Vasodilation in Hypercholesterolemic Humans", American Society for Clinical Investigation, vol. 90, Oct. 1992, 1248-1253.
Malinski et al., "Nitric oxide release form a single cell measured in situ by a porphyrinic-based microsensor", Letters to Nature, vol. 358, Aug. 20, 1992.
Drexler et al., "Endothelial Function in Chronic Congestive Heart Failure", Am J Cardiol 69:1596-1601, 1992.

Taddei et al, "Endothelium-Dependent Forearm Vasodilation Is Reduced in Normotensive Subjects with Familial History of Hypertension", Journal of Cardiovascular Pharmacology, (Suppl 12):S193-S195, 1992.

Calver et al., "Effect of local intra-arterial $N^G$-monomethyl-L-arginine in patients with hypertension: the nitric oxide dilator mechanism appears abnormal", Journal of Hypertension, 10:1025-1031, 1992.

Eighth Scientific Meeting of the American Society of Hypertension, #1280 "Ambulatory Blood Pressure Monitoring (ABPM) to Assess the Hypertensive Effects of Nebivolol (N) and Hydrochlorothiazide (HCTZ) Monotherapies and Combinations in Truly Hypertensive Patients", New York, New York, USA (May 19-22, 1993); American Journal of Hypertension 6 (5, part 2) p. 100A.

Ford, G.A.; "Endothelial Dependent Venodilatory Action Of Nebivolol In Human Hand Veins"; 6th European Meeting on Hypertension, Milan, Italy, Jun. 4-7, 1993; pp. 239-240.

Lafabvre, J., et al; "Evaluation Du Nebivolol Et/Ou De L'Hydrochlorothiazide vs Placebo Par Moniteur Ambulatoire: Devis Plurifactoriel"; Formule De Resume; (Oct. 20, 1993); 1 pg.

Van Bortel, L. M. A. B. V.; Beyond the tension of hypertension focus on non-antihypertensive aspects of antihypertensive treatment Janssen Research Foundation Publication (Nov. 18, 1993).

Taddei, et al., "Vasodilation to Acetylcholine in Primary and Secondary Forms of Human Hypertension", Hypertension 1993; 21:929-933.

Casino, et al., "The Role of Nitric Oxide in Endothelium-Dependent Vasodilation of Hypercholerterolemic Patients", Circulation, 1993;88:2541-2547.

Ohara et al., "Hypercholesterolemia Increases Endothelial Superoxide Anion Production", J. Clin. Invest. 91:2546-2551, 1993.

Lacourciere, et al., "Ambulatory blood pressure monitoring to assess the antihypertensive effects of nebivolol and hydrochlorotriazide monotherapies and combinations in truly hypertensive patients", Amer. J. Hypertension 6: p. 100A, 1993.

Lacourciere, and Arnott "Effects of nebivolol and low-dose hydrochlorothiazide on lipid metabolism", J. Hypertension 12 (Suppl 3) p. 12, 1994.

Lacourciere, Yves, et al.; "Placebo-controlled comparison of the effects of nebivolol and low-dose hydrochlorothiazide as monotherapies and in combination on blood pressure and lipid profile in hypertensive patients"; Journal of Human Hypertension (1994) 8, pp. 283-288.

Bowman, et al., "Nitric oxide mediated venodilator effects of nebivolol", British Journal of Clinical Pharmacology, 1994, 38:199-204.

Lacourciere, Yves, et al., "Treatment of Ambulatory Hypertensives with Nebivolol or Hydrochlorothiazide Alone and in Combination"; American Journal of Hypertension, Ltd. (Feb. 1994) 7:137-145.

15th Scientific Meeting of the ISOH, Melbourne, Australia (Mar. 20-24, 1994); Journal of Hypertension 12 (Suppl. 3) p. 12; "Effects of Nebivolol and Low Doses of Hydrochlorothiazide of LIPID Metabolism, A Placebo-Controlled Comparison".

Cockcroft,et al., "Nebivolol vasodilates human forearm vasculature: Evidence for an L-arginine/NO-dependent mechanism", Journal of Pharmacology and Experimental Therapeutics, 1995, 274: 1067-1071.

Treasure, et al., "Beneficial Effects of Cholesterol-Lowering Therapy on the Coronary Endothelium in Patients with Coronary Artery Disease", The New England Journal of Medicine, vol. 332, No. 8, Feb. 23, 1995.

Anderson, et al. "The effect of cholesterol-lowering and antioxidant therapy on endotheoium-dependent coronary vasomotion", The New England Journal of Medicine, vol. 332, No. 8, Feb. 23, 1995.

Kamal, F. et al.; "The effects of ranitidine and cimetidine on the pharmacokinetics and pharmacodynamics of nebivolol"; Proc. Brit. Pharm. Soc., Oxford, UK, Jul. 12-14, 1995; pp. 519P-520P.

Liao, et al., "Oxidized Low-density Lipoprotein Decreases the Expression of Endothelial Nitric Oxide Synthase", The Journal of Biological Chemistry, vol. 270, No. 1, pp. 319-324, Jan. 1995.

Burt et al., "Prevalance of Hypertension in the US Adult Population", Hypertension, 25:305-313, 1995.

Münzel, et al., "Evidence for Enhanced Vascular Superoxide Anion Production in Nitrate Tolerance", J. Clin. Invest. 95:187-194, 1995.

Quyyumi, et al., "Contribution of Nitric Oxide to Metabolic Coronary Vasodilation in the Human Heart", Circulation, 92:320-326, 1995.

Mancini, et al., "Angiotensin-Converting Enzyme Inhibition with Quinapril Improves Endothelial Vasomotor Dysfunction in Patients with Coronary Artery Disease", Circulation, 94:258-265, 1996.

Kugiyama, et al., "Nitric Oxide Activity Is Deficient in Spasm Arteries of Patients with Coronary Spastic Angina", Circulation, 94:266-272, 1996.

Rajagopalan, et al., "Angiotensin II-mediated Hypertension in the Rat Increases Vascular Superoxide Production via Membrane NADH/NADPH Oxidase Activation", The Journal of Clinical Investigation, Vo. 97, No. 8, Apr. 1996.

Iadecola, et al., "Inducible Nitric Oxide Synthase Gene Expression in Vascular Cells after Transient Focal Cerebral Ischemia", Stroke, 27:1373-1380, 1996.

Münzel, et al., "Hydralazine Prevents Nitroglycerin Tolerance by Inhibiting Activation of a Membrane-bound NADH Oxidase", The Journal of Clinical Investigation, vol. 98, No. 6, 1465-1470, 1996.

Shesely et al., "Elevated blood pressures in mice lacking endothelial nitric oxide synthase", Proc Natl Acad Sci USA, vol. 93, pp. 13176-13181, Nov. 1996.

Tschundi, et al., "Effect of Age on Kinetics of Nitric Oxide Release in Rat Aorta and Pulmonary Artery", The American Society for Clinical Investigation, vol. 98, No. 4, pp. 899-905, Aug. 1996.

Mason, et al., "Effect of Oxidative Stress on Membrane Structure: Small-angle X-ray diffraction analysis", Free Radical Biology & Medicine, vol. 23, No. 3, pp. 419-425, 1997.

Pieper, Galen M., "Acute Amelioration of Diabetic Endothelial Dysfunction with a Derivative of the Nitric oxide Synthase Cofactor, Tetrahydrobiopterin", Journal of Cardiovascular Pharmacology, 29:S-15, 1997.

Harrison, David G., Perspective Series: Nitric Oxide and Nitric Oxide Synthases, "Cellular and Molecular Mechanism of Endothelial Cell Dysfunction", American Sociey for Clinical Investigation, vol. 100, No. 9, Nov. 1997.

Janssens, W.J., et al.; Symposium on: Endothelium in Hypertension, New Therapeutic Trends, "Pharmacology and pharmacokinetics of nebivolol"; Symposium on Endothelium in Hypertension, Berlin, Germany (Mar. 1, 1997) pp. 10-13.

Lvovich, et al., "Amperometric Sensors for Simultaneous Superoxide and Hydrogen Peroxide Detection", Analyticla Chemistry, vol. 69, No. 3, Feb. 1997.

Forte et al., "Basal nitric oxide synthesis in essential hypertension", Lancet 1997; 349:837-42.

Stein, et al., "Vasodilation in black Americans: Attenuated nitric oxide mediated responses", Pharmacodynamics and Drug Action, Clin Pharmacol Ther 62:436-43, 1997.

Pitei, et al., "NO-dependent Smooth Muscle Vasodilatation is Reduced in NIDDM Patients with Peripheral Sensory Neuropathy", Diabetic Medicine, 14:284-290, 1997.

Kinoshita, et al., "Inhibition of tetrahydrobiopterin biosynthesis impairs endothelium-dependent relaxations in canine basilar artery", Tetrahydrrobiopterin Availabity and Endothelium, 1997.

Bouloumié et al., "Endothelial Dysfunction Coincides with an Enhanced Nitric Oxide Synthase Expression and Superoxide Anion Production", Hypertenion, 30:934-941, 1997.

McIntyre et al., "Sex Differences in the Abundance of Endothelial Nitric Oxide in a Model of Genetic Hypertension", Hypertension, 30:1517-1524, 1997.

Mohri et al., "Basal Release of Nitric Oxide is Decreased in the Coronary Cirulation in Patients with Heart Failure", Hypertension, 30:50-56, 1997.

Böger, et al., "Dietary $_L$-Arginine Reduces the Progression of Atherosclerosis in Cholesterol-Fed Rabbits", Circulation, 96:1282-1290, 1997.

Huk, et al., "$_L$-Arginine Treatment Alters the Kinetics of Nitric Oxide and Superoxide Release and Reduces Ischemia/Reperfusion Injury in Skeletal Muscle", Circulation, 96:667-675, 1997.

Zhang, et al., "Amlodipine Releases Nitric Oxide From Canine Coronary Microvessels", Circulation, 97:576-580, 1998.

Vidal et al., "Atherogenic concentrations of native low-density lipoproteins down-regulate nitric-oxide-synthase mRNA and protein levels in endothelial cells", Eur J Biochem, 252, 378-384 (1998).

Mason, et al., "Antioxidant and Cytoprotective Activities of the Calcium Channel Blocker Mibefradil", Biochemical Pharmacology, vol. 55, pp. 1843-1852, 1998.

Laufs, et al., "Upregulation of Endothelial Nitric oxide Synthase by HMG $C_oA$ Reductase Inhibitors", Circulation, 1998; 97:1129-1135.

Kurtz et al., "Role of nitric oxide in the control of rennin secretion", American Physiological Society, 1998.

Oemar, et al., "Reduced Endothelial Nitric Oxide Synthase Expression and Production in Human atherosclerosis", Circulation, 97:2494-2498, 1998.

Tulenko, et al., "Physical effects of cholesterol on arterial smooth muscle membranes: evidence of immiscible cholesterol domains and alterations in bilayer width during atherogenesis", Journal of Lipid Research, vol. 39, 1998.

Liao, "Endothelium and acute coronary syndromes", Clinical Chemistry, 44:8(B) 1799-1808, 1998.

Monbouli et al., "Endothelial Dynsfunction: From Physiology to Therapy", J Moll Cell Cardiol 31:61-74, 1999.

Dawes, et al., "The vasodilator action of nebivolol in forearm vasculature of subjects with essential hypertension", British Journal of Clinical Pharmacology, 1999, 48:460-463.

Cases, "Clinical Pharmacology of Nebivolol" Drugs of Today 1999, 35 (9); pp. 685-699.

McNeely, W. et al.; "Nebivolol in the Management of Essential Hypertension\ Review"; ADIS Drug Evaluation (Apr. 1999) 57 (4); pp. 633-651.

Freitag, A: "Nebivolol, a beta adrenoceptor antagonist with vasodilating effect"; Pharmazeutische Zeitung Dec. 16, 1999, Germany, vol. 144, No. 50.

Janssen, et al., "Transient and sustained impacts of hydroxyl radicals on sarcoplasmic reticulum function: protective effects of nebivolol", European Journal of Pharmacology, 1999, 366:223-232.

Kakoki, et al., "Effects of vasodilatory beta-adrenoceptor antagonists on endothelium-derived nitric oxide release in rat kidney", Hypertension, Jan. 1999, 33(1, Pt. 2): 467-71.

Brovkovych et al., "Nitric Oxide Release from Normal and Dysfunctional Endothelium", Journal of Physiology and Pharmacology, 50, 4, 575-586, 1999.

Kellner-Weibel, et al., "Crystallization of Free Cholesterol in Model Macrophage Foam Cells", Arterioscler Thromb Vasc Biol., 19:1891-1898, 1999.

Broeders, et al., "Nebivolol: a third-generation β-blocker that augments vascular nitric oxide release: endothelial beta(2)-adrenergis receptor-mediated nitric oxide production", Circulation, 2000, 102:677-684.

Schachter, M.; "Nevivolol: how different, how interesting?"; British Journal of Cardiology 7 (6), pp. 341, 343, 345, 347 (2000).

Buga et al., Nitric Oxide: Biology and Chemistry Abstracts; vol. 4, No. 3; p. 182 (2000); Academic Press, "Nebivolol: a possible novel mechanism in hypertension?"; Drugs & Therapy Perspectives.

Drugs & Therapy Perspectives; "Nebivolol: A possible novel mechanism in hypertension"; vol. 16, No. 5 (2000).

Erne, P.: "Nebivolol"; Pharma-Kritik 2000 Switzerland, vol. 22, No. 8, 2000, pp. 31-32.

Parenti et al., "Inositol phosphate metabolism and nitric-oxide synthase activity in endothelial cells are involved in the vasorelaxant activity of nebivolol", J Pharmacol Exp Ther, Feb. 2000; 292(2):698-703.

Perregaux, et al., "Brachial Vascular Reactivity in Blacks", Hypertension, 2000, 36:866-871.

Wagner, et al., "Improvement of Nitic Oxide-Dependent Vasodilatation by HMG-CoA Reductase Inhibitors Through Attenuation of Endothelial Superoxide Anion Formation", Arterioscler Thromb Vasc Biol, 20:61-69, 2000.

John, et al., "Impaired endothelial function in arterial hypertension and hypercholesterolemia: potential mechanisms and differences", Journal of Hypertension, 18:363-374, 2000.

Van Der Loo, et al., "Enhanced Peroxynitite Formation Is Associated with Bascular Aging", J Exp Med, Vo. 192, No. 12, Dec. 18, 2000.

Verganani et al., "Effect of Native and Oxidized Low-Density Lipoprotein on Endothelial Nitric Oxide and Superoxide Production", Circulation, 101:1261-1266, 2000.

Troost, et al., "Nebivolol decreases systemic oxidative stress in healthy volunteers", J. Clin Pharmacol. 50:377-379, 2000.

Xue, et al., "Amperometric Ultramicrosensors for Peroxynitrite Detection and Its Application toward Single Myocardial Cells", Amer. Chem. Society, 72: 5313-5321, 2000.

Gosgnach, W., et al.; "Nebivolol Induces Calcium-Independent Signaling in Endothelial Cells by a Possible β-Adrenergic Pathway"; Journal of Cardiovascular Pharmacology, vol. 38, No. 2, 2001; pp. 191-199.

10th International Congress on Cardiovascular Pharmacotherapy, Kyoto, Japan (Mar. 27-31, 2001); "Beneficial Effects of Combined Therapy Nebivolol Trimetazidine vs. Only Trimetazidine in Heart Failure"; Cardiovascular Drugs and Therapy 15 (Suppl. 1) p. 112.

Tzemos, Nikolaos, et al.; "Nebivolol Reverses Endothelial Dysfunction in Essential Hypertension"; Circulation 104:511-514 (Jun. 8, 2001).

Asanuma et al., "Benidipine, a Long-acting Ca Channel Blocker, Limits Infarct Size via Bradykinin- and NO-Dependent Mechanisms in Canine Hearts", Cardiovascular Drugs & Therapy, 15 225-231, 2001.

Paniagua, et al., Role of Endothelial Nitric Oxide in Shear Stress-Induced Vasodilatino of Human Microvasculature, Circulation, 103:1752-1758, 2001.

Loscalzo, Joseph, "Nitric oxide insufficiency, platelet activation, and arterial thrombosis", Circulation Research, 88:756-762, 2001.

Martinez-Gonzales et al., "3-Hydroxy-3-Methylglutaryl Coenzyme A Reductase Inhibition Prevents Endothelial NO Synthase Downregulation by Atherogenic levels of Native LDLs", Arterioscler Thromb Vasc Biol., 21:804-809, 2001.

Napoli, et al., "Nitric Oxide and Atherosclerosis", Nitric Oxide: Biology & Chemistry vol. 5, No. 2, pp. 88-97, 2001.

Feron et al., Hydroxy-Methylglutaryl-CoEnzyme A Reductase Inhibition Promotes Endothelial Nitric Oxide Synthase Activation Through a Decease in Caveolin Abundance, Circulation, 103:113-118, 2001.

Falciani et al., "Effects of Nebivolol on Human Platelet Aggregation", Journal of Cardiovascular Pharmacology, 38:922-929, 2001.

Tanus-Santos, et al., "Effects of ethnicity on the distribution of clinically relevant endothelial nitric oxide variants", Pharmacogenetics, 719-725, 2001.

Liu et al., "Effect of ACE Inhibitors and Angiotensin II Type 1 Receptor Antagonists on Endothelial NO Synthase Knockout Mice with Heart Failure", Hypertension, 39[part 2]:375-381, 2002.

Zou, et al., "Oxidation of the zinc-thiolate complex and uncoupling of endothelial nitric oxide synthase by peroxynitrite", J Clin Invest, 109:817-826, 2002.

Gol'Drin, et al., "Effect of enape combined with nebilet in hypertension", Lik Sprava, 2002, (7): 104-7.

Chlopicki, et al., "No-Dependent Vasodilation Induced by Nebivolol in Coronary Circulation is not Mediated by β-Adrenoceptors or by 5 $HT_{1A}$-Receptors", Journal of Physiology and Pharmacology 2002, 53, 4, 615-624.

Sica, Dominic; Review Article, Drugs 2002; "Rationale for Fixed-Dose Combinations in the Treatment of Hypertension";vol. 62, (3) p. 443-462.

Yakushin, S.S., et al.; "Assessment of the Safety and Antihypertensive Effectiveness of the Cardioselective Beta-Adrenoblocker Nebivolol in Patients with Arterial Hypertension Combined with Chronic Obstructive Bronchitis"; Kardiologiia 2002, 11:36-39.

Zadionchenko, V.S., et al.; "Effects of Nevibolol on Microcirculation, Platelet Aggregation and Blood Viscosity in Patients with Arterial Hypertension"; Kardiologiia 2002; 5:14-18.

Vertolli, U. et al.; "Eccentric LVH healing after starting renal replacement therapy" Journal of Nephrology 2002 Italy, vol. 15, No. 4, 2002, pp. 403-405.

Kalinowski, et al., "Angiotensin II $AT_1$ Receptor Antagonists Inhibit Platelet Adhesion and Aggregation by Nitric Oxide Release", Hypertension, vol. 40: 521-527, 2002.

Kalinowski, et al., "Cerivastatin Potentiates Nitric Oxide Release and Enos Expression Through Inhibition of Isoprenoids Synthesis", Journal of Physiology and Pharmacology 2002: 53-4: 585-595.

Gourine, et al., "Calcium Antagonist Clevidipine Reduces Myocardial Reperfusion Injury by a Mechanism Related to Bradykinin and Nitric Oxide", Journal of Cardiovascular Pharmacology, 40:564-570, 2002.

Landmesser, et al., "Role of p47$^{phox}$ in Vascular Oxidative Stress and Hypertension Caused by Antiotensin II", Hypertension, Oct. 2002.

Campia, et al., "Reduced Endothelium-Dependent and -Independent Dilation of Conductance Arteries in African Americans", Journal of American College of Cardiology vol. 40, No. 4, 2002.

Cosentino, et al., "Nitric oxide-mediated relaxations in salt-induced hypertension: effect of chronic $\beta_1$-selective receptor blockade", Journal of Hypertension, 20:421-428, 2002.

Pritchard, et al., "Native Low-Density Lipoprotein Induces Endothelial Nitric Oxide Synthase Dysfunction: Role of Heat Shock Protein 90 and Caveolin-1", Free Radical Biology & Medicine, vol. 33, No. 1, pp. 52-62, 2002.

Stepp, et al., "Native LDL and minimally oxidized LDL differentially regulate superoxide anion in vascular endothelium in situ", Am J Physiol Heart Circ Physical, 283:H750-H759, 2002.

Steinberg, et al., "Is the Oxidative Modification Hypothesis Relevant to Human Atherosclerosis?", Circulation, 105:2107-2111, 2002.

Ignarro, et al., "Nitric Oxide Donors and Cardiovascular Agents Modulating the Bioactivity of Nitric Oxide: An Overview", Circ. Res. 90:21-28, 2002.

Wassmann, et al., "Cellular Antioxidant Effects of Atorvastatin In Vitro and In Vivo", Arterioscler Thromb Vasc Biol., 22:300-305, 2002.

Bonetti et al., "Endothelial Dysfunction", Arterioscler Thromb Vasc Biol., 23:168-175, 2003.

Bundkirchen et al., "$\beta_1$-adrenoceptor selectivity of nebivolol and bisoprolol. A comparison of [$^3$H]CGP 12.177 and [$^{125}$I]iodocyanopindolol binding studies", European Journal of Pharmacology 460 (2003) 19-26.

Jialal, et al., "Antioxidants and Atherosclerosis: Don't Throw Out the Baby with the Bath Water", Circulation 2003: 107:926-928.

Alekseeva, et al., "The use of nebivolol in menopausal women with hypertension", Kardiologiia, 2003, 43(10): 72-5.

Karimova, et al., "Efficiency of combined nebivolol and enalapril therapy and their effect on regression of left ventricle hypertrophy", Uzbekiston Tibbiet Zhurnali, (1), 2003, 46-48.

Cominacini, et al., "Nebivolol and its 4-keto derivative increase nitric oxide in endothelial cells by reducing its oxidative inactivation", Am Coll Cardiol. Nov. 19, 2003, 42(10):1838-44.

Kalinowski, et al., "Third generation b-blockers stimulate nitric oxide release from endothelial cells through ATP efflux: a novel mechanism for antihypertensive action", Circulation, 2003, 107:2747-2752.

Mollnau, et al., "Nebivolol prevents vascular NOS III uncoupling in experimental hyperlipidemia and inhibits NADPH oxidase activity in inflammatory cells", Arteriosclerosis, Thrombosis, and Vascular Biology, 2003, 23:615-621.

Izzo, Joseph et al.; Izzo and Black; Hypertension Primer, Third Edition, "The Essentials of High Blood Pressure"; 2003 p. 408-429; (Chapter C138).

Amudha, K., et al.; "Ethnicity and Drug Therapy for Hypertension"; Current Pharmaceutical Design, 2003, 9; pp. 1691-1701; 2003 Bentham Science Publishers Ltd.

Rosei, E.A., et al.; "Evaluation of the Efficacy and Tolerability of Nebivolol versus—Lisinopril in the Treatment of Essential Arterial Hypertension: A Radomized, Multicentre", Double-blind Study; Blood Pressure 2003; 12 (Suppl. 1); 30-35.

Rizos, E., et al.; "The Combination of nebivolol plus pravastatin is associated with a more beneficial metabolic profile compared to that of atenolol plus pravastatin in hypertensive patients with dyslipidemia": a pilot study; Journal of Cardiovascular Pharmacology and Therapeutics, Jun. 2003 v8 i2 p. 127(8); Westminster Publications Inc.

Lazar et al., "Beneficial effects of combined therapy nebivolol trimetazidine, versus only trimetazidine in heart failure", Cardiovascular Drugs and Therapy 15 (Supple. 1) p. 112, 2001.

Gremmler, B. et al.; "Effects of AT1 receptor antagonist therapy in patients with severe heart failure pretreated with angiotensin-converting enzyme inhibitors"; Experimental and Clinical Cardiology 2003 Canada; vol. 7, No. 4, 2003, pp. 193-198.

Teoh, Y.P., et al.; "Candy in the clinic: Resistant hypertension in diabetes" British Journal of Diabetes and Vascular Disease 2003, United Kingdom, vol. 3, No. 4, 2003, pp. 300-301.

Katira and Chauhan "Nebivolol: A new beta blocker on the horizon" Indian Heart J 52:86-88, 2000.

Wing, et al. "Nebivolol and enalapril are not additive in combination in the treatment of essential hypertension" J. Hypertension 12 (Suppl. 3) p. 70, 1994.

Van De Water, et al. "Pharmacological and Hemodynamic Profile of Nebivolol, a chemically novel, potent, and selective B1-adrenergic antagonist" J. Cardiovascular Pharmacol 11: pp. 552-563, 1988.

Thai, et al., "Angiotensin Subtype 1 Receptor ($AT_1$) Blockade Improves Vasorelaxation in Heart Failure by Up-Regulation of Endothelial Nitric-Oxide Synthase via Activation of the $AT_2$ Receptor", Journal of Pharmacology and Experimental Therapeutics, Vop. 307, No. 3, 2003.

Landmesser, et al., "Oxidation of tetrahydrobioptgerin leads to uncoupling of endothelial cell nitric oxide synthase in hypertension", J Clin Invest 111:1201-1209, 2003.

Mason, et al., "Membrane Microdomains and Vascular Biology", Circulation, 107:2270-2273, 2003.

Ou, et al., "L-4F, an Apolipoprotein A-1 Mimetic, Restores Nitric Oxide and Superoxide Anion Balance in Low-Density Lipoprotein-Treated Endothelial Cells", Circulation, 107:1520-1524, 2003.

Rodriguez-Porcel et al., "Hypercholesterolemia and Hypertension Have Synergistic Deleterious Effects on Coronary Endothelial Function", Arterioscler Thromb Vasc Biol., 23:885-891, 2003.

Wolfrum et al., "Endothelium-Dependent Effects of Statins", Arterioscler Thromb Vasc Biol., 23:729-736, 2003.

Nissen et al., "Effect of Intensive Compared with Moderate Lipid-Lowering Therapy on Progression of Coronary Atherosclerosis", Amer. Med. Assoc., vol. 291, No. 9, 2004.

Mason, et al., "Effects of HMG-CoA Reductase Inhibitors on Endothelial Function", Circulation, 109[suppl. II]:II-34-II-41, 2004.

Tesloianu, et al., "Treatment of pulmonary hypertension in COPD: is there hope for the better?", Pneumologia (Bucharest, Romania), 53(4) :147-54, 2004.

Evdokimova, AG et al., "Nebivolol in the treatment of ischemic heart disease patients with chronic heart failure"; Database accession No. NLM15029131 abstract & KARDIOLOGIIA, 2004, vol. 44. No. 2, 2004, pp. 15-18; US National Library of Medicine (NLM), Bethesda, MD. US; 2004.

De Groot, et al., "Antioxidant activity of nebivolol in the rat aorta", Journal of Cardiovascular Pharmacology, 2004, 43:148-153.

Waring, W S, et al.; "Is There a need for novel antihypertensive therapies?"; Drug Discovery Today: Therapeutic Strategies, Elsevier, vol. 1, No. 2, Oct. 2004, pp. 143-148.

Cannon et al., "Intensive versus Moderate Lipid Lowering with Statins after Acute Coronary Syndromes", The New England Journal of Medicine, vol. 350, No. 15, Apr. 8, 2004.

Taylor, et al., "Combination of Isosorbide Dinitrate and Hydralazine in Blacks with Heart Failure", The New England Journal of Medicine, vol. 351, No. 20, Nov. 11, 2004.

Kalinowski, et al., "Race-Specific Differences in Endothelial Function", Circulation, 109:2511-2517, 2004.

Boydak, et al.; "A Randomised Comparison of the Effects of Nebivolol and Atenolol with and without Chlorthalidone on the Sexual Function of Hypertensive Men"; Clin. Drug Invest. 2005; 25(6) 409-416.

Petersen, et al., "Trends in medicine", American Society for Clinical Pharmacology and Therapeutics, Mar. 3-5, 2005.

Rosenkranz et al., "Phosphodiesterase type 5 inhibitor sildenafil citrate does not potentiate the vasodilative properties of nebivolol in rat aorta", Life Sciences 2005.

Mason et al., "Membrane location of nebivolol contributes to antioxidant activity and endothelial nitric oxide release in stroke-prone hypertensive rats", American Journal of Hypertension 18:181A, 2005.

Mason et al., "Nebivolol improves eNOS function and nitric oxide bioavailability in endothelial cells from African Americans", American Journal of Hypertension, 18:181A, 2005.

Mason et al., "Nebivolol reduces nitroxidative stress and restores nitric oxide bioavailability in endothelium of black Amerians", Circulation, 2005, 112:3795-3801.

Nissen, et al., Statin Therapy, LDL Cholesterol, C-Reactive Protein, and Coronary Artery Disease, The New England Journal of Medicine, Jan. 6, 2005.

Gunnett, et al., "Mechanisms of Inducible Nitric Oxide Synthase-Mediated Vascular Dynfunction", Arterioscler Tghromb Vasc Biol. 25:1617-1622, 2005.

Pasini, et al., "Nebivolol decreases oxidative stress in essential hypertensive patients and increases nitric oxide by reducing its oxidative inactivation", J Hypertens 23:589-596, 2005.

* cited by examiner

*$p < 0.05$ and †$p < 0.01$ vs preincubation with nebivolol alone (n = 6)

COMPOSITIONS COMPRISING NEBIVOLOL

This application is based on and claims priority from U.S. Provisional Patent Application Ser. No. 60/577,423, Eric Davis, John O'Donnell, Peter Bottini, filed Jun. 4, 2004.

TECHNICAL FIELD

This invention relates to compositions comprising nebivolol and one or more other active agent. More particularly, this invention relates to compositions comprising nebivolol and one or more cardiovascular agents for the treatment and/or prevention of cardiovascular diseases.

BACKGROUND OF THE INVENTION

Hypertension is a major health concern in the US. Approximately 50 million Americans have elevated blood pressure defined as a systolic blood pressure (SBP)$\geq$140 mmHg or a diastolic blood pressure (DBP) $\geq$90 mmHg. In addition, individuals with blood pressure of 120/80 mmHg or higher are at increased risk of developing hypertension and are considered to be in a "pre-hypertension" state. Severity of hypertension is currently classified by stage, with Stage 1 hypertension spanning blood pressure ranges from 140/90 to 159/99 mmHg and Stage 2 including blood pressures $\geq$160/100 mmHg.

Onset of hypertension (diastolic alone or in combination with systolic) typically occurs between 25 and 55 years of age. The risk of developing hypertension increases more dramatically with increasing age. According to the CDC, 68.3% of men aged 65-74 have hypertension in the U.S. (Health United States, 2003, CDC/National Center for Health Statistics) and 70.7% of men aged over 75 have hypertension in the U.S. (Health United States, 2003, CDC/National Center for Health Statistics). In addition, 73.4% of women aged 65-74 have hypertension in the US (Health United States, 2003, CDC/National Center for Health Statistics) and 84.9% of women aged over 75 have hypertension in the US (Health United States, 2003, CDC/National Center for Health Statistics).

Pharmaceutical formulations that stimulate, agonize, or potentiate endothelial nitric oxide production, particularly formulations that produce increased nitric oxide levels in African Americans, are needed.

SUMMARY OF THE INVENTION

In one aspect, the present invention features a pharmaceutical composition comprising nebivolol and at least one other active agent. In a further embodiment, at least one of the active agents is a cardiovascular agent. In a further embodiment, the at least one cardiovascular agent is selected from the group consisting of ACE inhibitors (angiotensin II converting enzyme inhibitors), ARB's (angiotensin II receptor antagonists), adrenergic blockers, adrenergic agonists, agents for pheochromocytoma, antiarrhythmics, antiplatelet agents, anticoagulants, antihypertensives, antilipemic agents, antidiabetics, antiinflammatory agents, calcium channel blockers, CETP inhibitors, COX-2 inhibitors, direct thrombin inhibitors, diuretics, endothelin receptor antagonists, HMG Co-A reductase inhibitors, inotropic agents, rennin inhibitors, vasodialators, vasopressors, AGE crosslink breakers (advanced glycosylation end-product crosslink breakers, such as alagebrium, see U.S. Pat. No. 6,458,819), and AGE formation inhibitors (advanced glycosylation end-product formation inhibitors, such as pimagedine), and mixtures thereof. In one embodiment, the other cardiovascular agent is an ACE inhibitor or an ARB. In a further embodiment, the other cardiovascular agent includes an ACE inhibitor and an ARB. In a further embodiment, the ACE inhibitor is selected from the group consisting of: alacepril, benazepril, captopril, ceronapril, cilazapril, delapril, enalapril, enalaprilat, fosinopril, imidapril, lisinopril, perindopril, quinapril, ramipril, ramiprilat, spirapril, temocapril, trandolapril. In a further embodiment, the ACE inhibitor is enalapril, ramipril, or ramiprilat. In a further embodiment, the other cardiovascular agent is an ARB selected from the group consisting of candesartan, eprosartan, irbesartan, losartan, valsartan.

In a further embodiment, the pharmaceutical composition comprises an amount of nebivolol in the range of between about 0.125 mg and about 40 mg. In a further embodiment, the amount of an ACE inhibitor may be in the range of between about 0.5 mg to about 80 mg, and/or the amount of ARB may be in the range of between about 1 mg and about 1200 mg.

In a further embodiment, the pharmaceutical composition comprises nebivolol and only one other active agent. In a further embodiment, the pharmaceutical composition comprises nebivolol and only one cardiovascular agent. In a further embodiment, the cardiovascular agent is selected from the group consisting of ACE inhibitors (angiotensin II converting enzyme inhibitors), ARB's (angiotensin II receptor antagonists), adrenergic blockers, adrenergic agonists, agents for pheochromocytoma, anti-anginal agents, antiarrhythmics, antiplatelet agents, anticoagulants, antihypertensives, antilipemic agents, antidiabetics, antiinflammatory agents, calcium channel blockers, CETP inhibitors, COX-2 inhibitors, direct thrombin inhibitors, diuretics, endothelin receptor antagonists, HMG Co-A reductase inhibitors, inotropic agents, rennin inhibitors, vasodialators, vasopressors, AGE crosslink breakers (advanced glycosylation end-product crosslink breakers, such as alagebrium, see U.S. Pat. No. 6,458,819), and AGE formation inhibitors (advanced glycosylation end-product formation inhibitors, such as pimagedine). In a further embodiment, the active agent is an ACE inhibitor or and ARB.

In another aspect, the present invention features a method of treating a subject for a cardiovascular disorder comprising administering to the subject an effective amount of nebivolol in combination with at least one other cardiovascular agent. In a further embodiment, the cardiovascular disorder is selected from the group consisting of atherosclerosis, hypertension, diabetes mellitus, hyperhomocysteinemia, heart failure, and renal failure.

In another aspect, the present invention features a method of preventing a cardiovascular disorder comprising administration to a subject an effective amount of nebivolol in combination with an effective amount of at least one other cardiovascular agent. In a further embodiment, the cardiovascular disorder is selected from the group consisting of congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, cardiac edema, renal insufficiency, nephrotic edema, hepatic edema, stroke, transient ischemic attacks, cerebrovascular accidents, restenosis, controlling blood pressure in hypertension, platelet adhesion, platelet aggregation, smooth muscle cell proliferation, pulmonary edema, and vascular complications associated with the use of medical devices.

In another aspect, the present invention features a kit comprising an effective amount of nebivolol in combination with an effective amount of another cardiovascular agent.

Even though nebivolol has β-blocking properties, nebivolol is different from other classic β-blockers in that it is highly selective to the β1 adrenergic receptors and also has vasodilating effects related to its effect on endothelial nitric oxide. It is believed that nebivolol increases the levels of nitric oxide within the vascular endothelium through the L-arginine-nitric oxide pathway and has been shown to improve endothelial dysfunction and improve compliance of blood vessels. Nebivolol has also been shown to have antioxidant characteristics which are favorable to the normal functioning of the vascular endothelium. These characteristics make nebivolol an effective antihypertensive agent with favorable effects on the vascular endothelium and cardiovascular system. Nebivolol has been shown to be beneficial in the treatment of cardiovascular diseases such as hypertension, congestive heart failure, arterial stiffness and endothelial dysfunction. In part, the present invention features a composition comprising nebivolol and another cardiovascular agent that is believed to work via a different mechanism.

These embodiments of the present invention, other embodiments, and their features and characteristics, will be apparent from the description, drawings and claims that follow.

DETAILED DESCRIPTION OF THE INVENTION

Definitions

Figure 1:
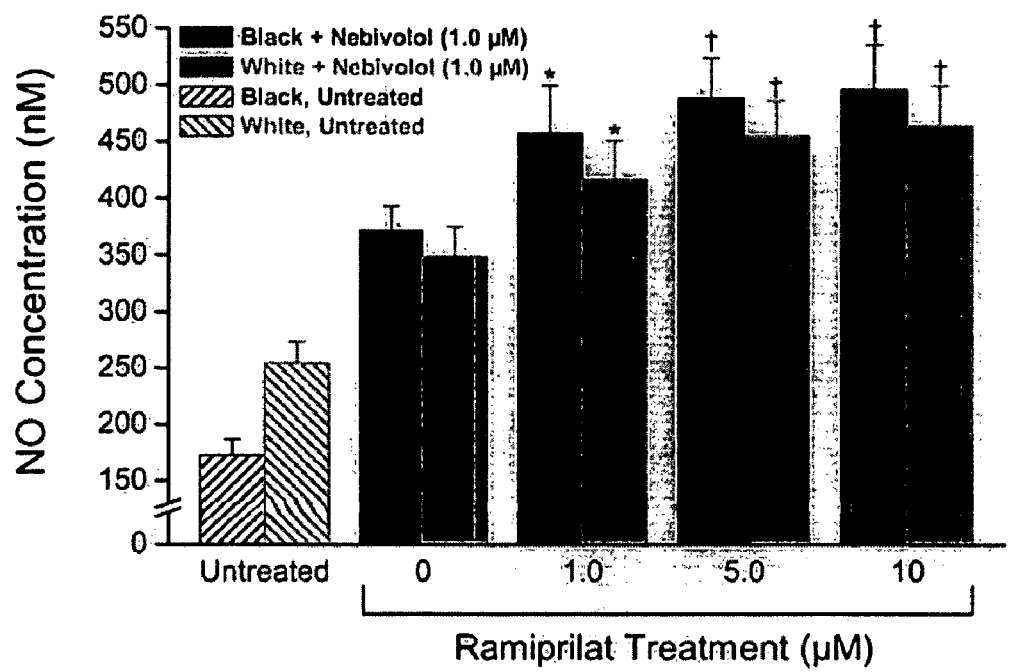
FIG. 1 depicts a comparison of NO release from Black and White donor endothelial cells after chronic treatment with ramprilat followed by treatment with nebivolol (1 μM).
Figure 2:
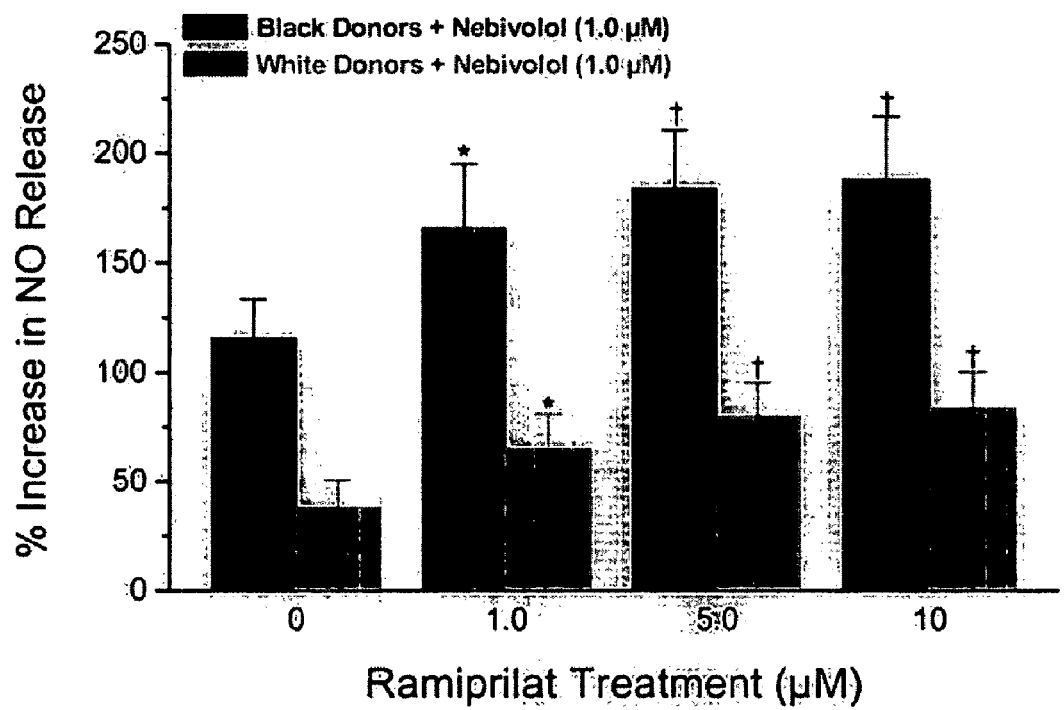
FIG. 2 depicts a comparison of the increase in NO release from Black and White donor endothelial cells after chronic treatment with ramiprilat followed by treatment with nebivolol (1 μM).

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e., to at least one) of the grammatical object of the article. By way of example, "an element" means one element or more than one element.

The phrase "angiotensin converting enzyme inhibitor" or "ACE inhibitor" as used herein refers to a compound that inhibits any enzyme from converting angiotensin to any other form.

The phrase "angiotensin II receptor antagonist" or "ARB" refers to a compound that binds to a receptor site on angiotensin II but does not cause any physiological changes unless another receptor ligand is present.

The term "antagonist" is art-recognized and refers to a compound that binds to a receptor site, but does not cause a physiological change unless another receptor ligand is present.

The term "bioavailable" is art-recognized and refers to a form of the subject invention that allows for it, or a portion of the amount administered, to be absorbed by, incorporated to, or otherwise physiologically available to a subject or patient to whom it is administered.

The phrase "cardiovascular agent" or "cardiovascular drug" refers to a therapeutic compound that is useful for treating or preventing a cardiovascular disease. Non-limiting examples of suitable cardiovascular agents include ACE inhibitors (angiotensin II converting enzyme inhibitors), ARB's (angiotensin II receptor antagonists), adrenergic blockers, adrenergic agonists, agents for pheochromocytoma, antianginal agents, antiarrhythmics, antiplatelet agents, anticoagulants, antihypertensives, antilipemic agents, antidiabetics, antiinflammatory agents, calcium channel blockers, CETP inhibitors, COX-2 inhibitors, direct thrombin inhibitors, diuretics, endothelin receptor antagonists, HMG Co-A reductase inhibitors, inotropic agents, rennin inhibitors, vasodialators, vasopressors, AGE crosslink breakers (advanced glycosylation end-product crosslink breakers, such as alagebrium, see U.S. Pat. No. 6,458,819), and AGE formation inhibitors (advanced glycosylation end-product formation inhibitors, such as pimagedine), and combibations thereof.

Cardiovascular disease or disorder refers to any cardiovascular disease or disorder known in the art, including, but not limited to, wherein the cardiovascular disease is selected from the group consisting of congestive heart failure, hypertension, pulmonary hypertension, myocardial and cerebral infarctions, atherosclerosis, atherogenesis, thrombosis, ischemic heart disease, post-angioplasty restenosis, coronary artery diseases, renal failure, stable, unstable and variant (Prinzmetal) angina, cardiac edema, renal insufficiency, nephrotic edema, hepatic edema, stroke, transient ischemic attacks, cerebrovascular accidents, restenosis, controlling blood pressure in hypertension, platelet adhesion, platelet aggregation, smooth muscle cell proliferation, pulmonary edema, and vascular complications associated with the use of medical devices.

The term "combination" refers to two or more different active agents which are administered at roughly about the same time (for example, where the active agents are in a single pharmaceutical preparation) or at different times (for example, one agent is administered to the subject before the other).

The terms "drug," "pharmaceutically active agent," "bioactive agent," "therapeutic agent," and "active agent" may be used interchangeably and refer to a substance, such as a chemical compound or complex, that has a measurable beneficial physiological effect on the body, such as a therapeutic effect in treatment of a disease or disorder, when administered in an effective amount. Further, when these terms are used, or when a particular active agent is specifically identified by name or category, it is understood that such recitation is intended to include the active agent per se, as well as pharmaceutically acceptable, pharmacologically active derivatives thereof, or compounds significantly related thereto, including without limitation, salts, pharmaceutically acceptable salts, N-oxides, prodrugs, active metabolites, isomers, fragments, analogs, solvates hydrates, radioisotopes, etc.

The phrase "effective amount" refers to that amount of a substance that produces some desired local or systemic effect at a reasonable benefit/risk ratio applicable to any treatment.

The effective amount of such substance will vary depending upon the subject and disease condition being treated, the weight and age of the subject, the severity of the disease condition, the manner of administration and the like, which can readily be determined by one of ordinary skill in the art.

"Endothelial dysfunction" refers to the impaired ability of in any physiological processes carried out by the endothelium, in particular, production of nitric oxide regardless of cause. It may be evaluated by, such as, for example, invasive techniques, such as, for example, coronary artery reactivity to acetylcholine or methacholine, and the like, or by noninvasive techniques, such as, for example, blood flow measurements, brachial artery flow dilation using cuff occlusion of the arm above or below the elbow, brachial artery ultrasonography, imaging techniques, measurement of circulating biomarkers, such as, asymmetric dimethylarginine (ADMA), and the like. For the latter measurement the endothelial-dependent flow-mediated dialation will be lower in patients diagnosed with an endothelial dysfunction.

The phrase "endothelial nitric oxide synthase" or "eNOS" refers to enzymes that produce nitric oxide The phrase "nebivolol composition" refers to a composition comprising nebivolol. Nebivolol is a mixture of d and l isomers of α,α-'-[iminobismethylene]bis[6-fluoro-3,4-dihydro-2H-1-benzopyran-2-methanol]. The composition may include at least one other cardiovascular agent or at least one pharmaceutically acceptable carrier or both. A "patient," "subject" or "host" may be a human or non-human animal.

The term "pharmaceutically acceptable salts" is art-recognized and refers to the relatively non-toxic, inorganic and organic acid addition salts of compounds, including, for example, those contained in compositions of the present invention.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof from one organ, or portion of the body, to another organ, or portion of the body. Each carrier must be acceptable in the sense of being compatible with the subject composition and its components and not injurious to the patient. Some examples of materials which may serve as pharmaceutically acceptable excipients include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) IV fluids, including but not limited to Ringer's solution, 5% dextrose in water, and half normalsaline; (19) ethyl alcohol; (20) phosphate buffer solutions; and (21) other non-toxic compatible substances employed in pharmaceutical formulations.

The term "prophylactic" or "therapeutic" treatment is art-recognized and refers to administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if administered after manifestation of the unwanted condition, the treatment is therapeutic (i.e., it is intended to diminish, ameliorate or maintain the existing unwanted condition or side effects therefrom).

The term "structure-activity relationship" or "(SAR)" is art-recognized and refers to the way in which altering the molecular structure of a drug or other compound alters its interaction with a receptor, enzyme, nucleic acid or other target and the like.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

The term "synthetic" is art-recognized and refers to production by in vitro chemical or enzymatic synthesis.

The phrase "therapeutic effect" is art-recognized and refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and/or conditions in an animal or human. The phrase "therapeutically-effective amount" means that amount of such a substance that produces some desired local or systemic effect at a reasonable benefit/risk ratio applicable to any treatment. The therapeutically effective amount of such substance will vary depending upon the subject and disease condition being treated, the weight and age of the subject, the severity of the disease condition, the manner of administration and the like, which can readily be determined by one of ordinary skill in the art.

The term "treating" is art-recognized and refers to curing as well as ameliorating at least one symptom of any condition or disease.

Nebivolol

Nebivolol is a β-receptor blocking drug that is a mixture of d- and l-enantiomers, of which d-nebivolol is a highly selective $β_1$-receptor antagonist.

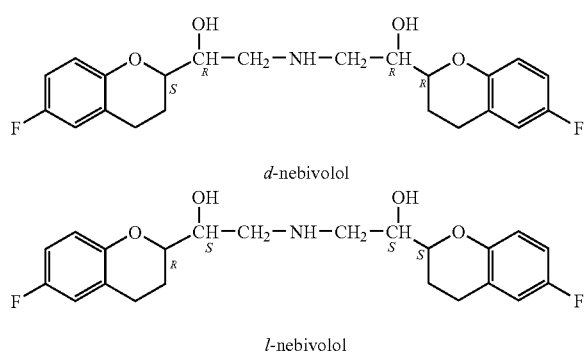

*d*-nebivolol

*l*-nebivolol

In addition to its β-receptor blocking properties, nebivolol has been shown to cause endothelium-dependent vasodilation in both normotensive and hypertensive subjects. Cockcroft J R, Chowienczyk P J, Brett S E, Chen C P, Dupont A G, Nueten L V, Wooding S J, Ritter J M., *Journal of Pharmacology and Experimental Therapeutics*. 1995;274:1067-1071; Tzemos N, Lim P O, MacDonald T M., *Circulation*, 2001; 104:511-514; Broeders M A, Doevendans P A, Bekkers B C, Bronsaer R, van Gorsel E, Heemskerk J W, Egbrink M G, van Breda E, Reneman R S, van Der Zee R., *Circulation*. 2000; 102:677-684. In experimental models, nebivolol has been demonstrated to stimulate NO release through $β_2$-adrenergic receptor-mediated NO production and/or ATP efflux with consequent stimulation of P2Y-purinoceptor-mediated NO release. Broeders M A, Doevendans P A, Bekkers B C, Bronsaer R, van Gorsel E, Heemskerk J W, Egbrink M G, van Breda E, Reneman R S, van Der Zee R., *Circulation*, 2000; 102:677-684; Kalinowski L, Dobrucki L W, Szczepanska-Konkel M, Jankowski M, Martyniec L, Angielski S, Malinski T., *Circulation*, 2003;107:2747-2752. It has also been reported that nebivolol inhibits NO synthase uncoupling and produces systemic antioxidant effects. Mollnau H, Schulz E, Daiber A, Baldus S, Oelze M, August M, Wendt M, Walter U, Geiger C, Agrawal R, Kleschyov A L, Meinertz T, Thomas Münzel T., *Arteriosclerosis, Thrombosis, and Vascular Biology*. 2003;23:615-621; Troost R, Schwedhelm E, Rojczyk S, Tsikas D, Frolich J C., *British Journal of Clinical Pharmacology*, 2000;50:377-379.

Compositions Comprising Nebivolol

In part, the present invention features compositions comprising nebivolol and at least one other active agent, wherein the at least one other active agent is a cardiovascular agent. The amount of each cardiovascular agent present in the compositions may vary depending on a number of variables such as age, weight, gender, and health related issues. In general, the dosage of the cardiovascular agents will generally be in the range of about 0.01 ng to about 10 g per kg body weight, specifically in the range of about 1 ng to about 0.1 g per kg, and more specifically in the range of about 100 ng to about 10 mg per kg. In another embodiment, the amount of nebivolol in the compositions of the present invention may be anywhere from about 0.125 mg to about 40 mg. In one example, when the other cardiovascular agent is an ACE inhibitor, the amount of the ACE inhibitor may be anywhere from 0.5 mg to about 80 mg. When the other cardiovascular agent is an ARB, the amount of ARB may be anywhere from about 1 mg to about 1200 mg. The amount of the other cardiovascular agent will depend in part on the particular cardiovascular agent used.

In addition to ACE inhibitors and ARBs, additional cardiovascular agents include, but are not limited to adrenergic blockers, adrenergic agonists, agents for pheochromocytoma, antianginal agents, antiarrhythmics, antiplatelet agents, anticoagulants, antihypertensives, antilipemic agents, antidiabetics, antiinflammatory agents, calcium channel blockers, CETP inhibitors, COX-2 inhibitors, direct thrombin inhibitors, diuretics, endothelin receptor antagonists, HMG Co-A reductase inhibitors, inotropic agents, rennin inhibitors, vasodialators, vasopressors, AGE crosslink breakers (advanced glycosylation end-product crosslink breakers, such as alagebrium, see U.S. Pat. No. 6,458,819), and AGE formation inhibitors (advanced glycosylation end-product formation inhibitors, such as pimagedine). Cardiovascular agents falling within these general categories are exemplified by the following:

"Angiotensin I Converting Enzymes (ACE's) and Angiotensin II Receptor Antagonists (ARB's)"

"Angiotensin II receptor antagonists" (ARB's) are compounds which interfere with the activity of angiotensin II by binding to angiotensin II receptors and interfering with its activity. Angiotensin I and angiotensin II are synthesized by the enzymatic renin-angiotensin pathway. The synthetic process is initiated when the enzyme renin acts on angiotensinogen, a pseudoglobulin in blood plasma, to produce the decapeptide angiotensin I. Angiotensin I is converted by angiotensin converting enzyme (ACE) to angiotensin II (angiotensin-[1-8]octapeptide). The latter is an active pressor substance which has been implicated as a causative agent in several forms of hypertension in various mammalian species, e.g., humans.

Angiotensin II receptor antagonists (ARB's) are well known and include peptide compounds and non-peptide compounds. Most angiotensin II receptor antagonists are slightly modified congeners in which agonist activity is attenuated by replacement of phenylalanine in position 8 with some other amino acid; stability can be enhanced by other replacements that slow degeneration in vivo.

Examples of angiotensin II receptor antagonists include: peptidic compounds (e.g., saralasin and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl] 1H-imidazole-5-yl[methylane]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche A G); A.sub.2 agonists (Marion Merrill Dow) and certain non-peptide heterocycles (G. D. Searle and Company). Other non-limiting examples of ARBs include candesartan, eprosartan, irbesartan, losartan, and valsartan. Other ARBs may be identified using standard assaying techniques known to one of ordinary skill in the art.

"Angiotensin converting enzyme" (ACE) is an enzyme which catalyzes the conversion of angiotensin I to angiotensin II. ACE inhibitors include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril. Other non-limiting examples of ACE inhibitors include, but are not limited to, alacepril, benazepril, captopril, ceronapril, cilazapril, delapril, enalapril, enalaprilat, fosinopril, imidapril, lisinopril, perindopril, quinapril, ramipril, ramiprilat, spirapril, temocapril, trandolapril.

Adrenergic Blockers

Non-limiting examples of adrenergic blockers, both α- and β-adrenergic blockers, that may be used in the compositions of the present invention include Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, sotalolnadolol, tiprenolol, tomalolol, timolol, bupranolol, penbutolol, trimepranol, yohimbine, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

Adrenergic Agonists

Non-limiting examples of adrenergic agonists, both α- and β-adrenergic agonists, that may be used in the compositions of the present invention include adrafinil, adrenalone, albuterol, amidephrine, apraclonidine, bitolterol, budralazine, carbuterol, clenbuterol, clonidine, clorprenaline, clonidine, cyclopentamine, denopamine, detomidine, dimetofrine, dioxethedrine, dipivefrin, dopexamine, ephedrine, epinephrine, etafedrine, ethylnorepinephrine, fenoterol, fenoxazoline, formoterol, guanabenz, guanfacine, hexoprenaline, hydroxyamphetamine, ibopamine, indanazoline, isoetharine, isometheptene, isoproterenol, mabuterol, mephentermine, metaproterenol, metaraminol, metazoline, methoxamine, methylhexaneamine, methoxyphenamine, midodrine, modafinil, moxonidine, naphazoline, norepinephrine norfenefrine, octodrine, octopamine, oxyfedrine, oxymetazoline, phenylephrine hydrochloride, phenylpropanolamine hydrochloride, phenylpropylmethylamine, pholedrine, pirbuterol prenalterol, procaterol, propylhexedrine, protokylol, pseudoephedrine, reproterol, rilmenidine, rimiterol, ritodrine, salmeterol, solterenol, synephrine, talipexole, terbutaline, tetrahydrozoline, tiamenidine, tramazoline, tretoquinol, tuaminoheptane, tulobuterol, tymazoline, tyramine, xamoterol, xylometazoline, and mixtures thereof.

Agents for Pheochromocytoma

Include but are not limited to chemotherapeutics.

Antiangina Agents

Include but are not limited to amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, nitrates (including but not limited to glyceryl trinitrate (GTN, nitroglycerin, Nitro-Bid), isosorbide dinitrate (ISDN, Isordil), isosorbide-5-mononitrate (5-ISMN, Ismo), amyl nitrate and nicorandil (Icorel)), primidolol, ranolazine hydrochoride, tosifen, verapamil hydrochloride).

Antiarrhythmics

Non-limiting examples of antiarrhythmics that may be used in the compositions of the present invention include acebutolol, acecainide, adenosine, ajmaline, alprenolol, amiodarone, amoproxan, aprindine, aprotinolol, atenolol, azimilide, bevantolol, bidisomide, bretylium tosylate, bucumolol, butetolol, bunaftine, bunitrolol, bupranolol, butidrine hydrochloride, butobendine, capobenic acid, carazolol, carteolol, cifenline, cloranolol, disopyramide, dofetilide, encainide, esmolol, flecainide, hydroquinidine, ibutilide, indecainide, indenolol, ipratropium bromide, lidocaine, lorajmine, lorcainide, meobentine, mexiletine, moricizine, nadoxolol, nifenaolol, oxprenolol, penbutolol, pentisomide, pilsicainide, pindolol, pirmenol, practolol, prajmaline, procainamide hydrochloride, pronethalol, propafenone, propranolol, pyrinoline, quinidine, sematilide, sotalol, talinolol, tilisolol, timolol, tocainide, verapamil, viquidil, xibenolol, and mixtures thereof.

Antiplatelet Agents

Non-limiting examples of antiplatelet agents that may be used in the compositions of the present invention include clopidogrel, dipyridamole, abcixamab, and ticlodipine.

Anticoagulants

Anti-coagulant agents are agents which inhibit the coagulation pathway by impacting negatively upon the production, deposition, cleavage and/or activation of factors essential in the formation of a blood clot. Non-limiting examples of anticoagulants (i.e, coagulation-related therapy) that may be used in the compositions of the present invention include Aggrenox, Agrylin, Amicar, Anturane, Arixtra, Coumadin, Fragmin, Heparin Sodium, Lovenox, Mephyton, Miradon, Persantine, Plavix, Pletal, Ticlid, Trental, Warfarin. Other "anti-coagulant" and/or "fibrinolytic" agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

Still other anti-coagulant agents include, but are not limited to, Ancrod; Anticoagulant Citrate Dextrose Solution; Anticoagulant Citrate Phosphate Dextrose Adenine Solution; Anticoagulant Citrate Phosphate Dextrose Solution; Anticoagulant Heparin Solution; Anticoagulant Sodium Citrate Solution; Ardeparin Sodium; Bivalirudin; Bromindione; Dalteparin Sodium; Desirudin; Dicumarol; Heparin Calcium; Heparin Sodium; Lyapolate Sodium; Nafamostat Mesylate; Phenprocoumon; Tinzaparin Sodium.

Inhibitors of platelet function are agents that impair the ability of mature platelets to perform their normal physiological roles (i.e., their normal function). Platelets are normally involved in a number of physiological processes such as adhesion, for example, to cellular and non-cellular entities, aggregation, for example, for the purpose of forming a blood clot, and release of factors such as growth factors (e.g., platelet-derived growth factor (PDGF)) and platelet granular components. One subcategory of platelet function inhibitors are inhibitors of platelet aggregation which are compounds which reduce or halt the ability of platelets to associate physically with themselves or with other cellular and non-cellular components, thereby precluding the ability of a platelet to form a thrombus.

Examples of useful inhibitors of platelet function include but are not limited to acadesine, anagrelide (if given at doses exceeding 10 mg/day), anipamil, argatroban, aspirin, clopidogrel, cyclooxygenase inhibitors such as nonsteroidal antiinflammatory drugs and the synthetic compound FR-122047, danaparoid sodium, dazoxiben hydrochloride, diadenosine 5',5'''-P 1,P4-tetraphosphate (Ap4A) analogs, difibrotide, dilazep dihydrochloride, 1,2- and 1,3-glyceryl dinitrate, dipyridamole, dopamine and 3-methoxytyramine, efegatran sulfate, enoxaparin sodium, glucagon, glycoprotein IIb/IIIa antagonists such as Ro-43-8857 and L-700,462, ifetroban, ifetroban sodium, iloprost, isocarbacyclin methyl ester, isosorbide-5-mononitrate, itazigrel, ketanserin and BM-13.177, lamifiban, lifarizine, molsidomine, nifedipine, oxagrelate, PGE, platelet activating factor antagonists such as lexipafant, prostacyclin (PGI.sub.2), pyrazines, pyridinol carbamate, ReoPro (i.e., abciximab), sulfinpyrazone, synthetic compounds BN-50727, BN-52021, CV-4151, E-5510, FK-409, GU-7, KB-2796, KBT-3022, KC-404, KF-4939, OP-41483, TRK-100, TA-3090, TFC-612 and ZK-36374, 2,4,5,7-tetrathiaoctane, 2,4,5,7-tetrathiaoctane 2,2-dioxide, 2,4,5-trithiahexane, theophyllin pentoxifyllin, thromboxane and thromboxane synthetase inhibitors such as picotamide and sulotroban, ticlopidine, tirofiban, trapidil and ticlopidine, trifenagrel, trilinolein, 3-substituted 5,6-bis(4-methoxyphenyl)-1,2,4-triazines, and antibodies to glycoprotein IIb/IIIa as well as those disclosed in U.S. Pat. No. 5,440,020, and antiserotonin drugs, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine.

Antihypertensives

Non-limiting examples of antihypertensives that may be used in the compositions of the present invention include amlodipine, benidipine, benezepril, candesartan, captopril, darodipine, dilitazem HCl, diazoxide, doxazosin HCl, enalapril, eposartan, losartan mesylate, felodipine, fenoldopam, fosenopril, guanabenz acetate, irbesartan, isradipine, lisinopril, mecamylamine, minoxidil, nicardipine HCl, nifedipine, nimodipine, nisoldipine, phenoxybenzamine HCl, prazosin HCl, quinapril, reserpine, terazosin HCl, telmisartan, and valsartan.

Antilipemic Agents

Non-limiting examples of antilipemic agents that may be used in the compositions of the present invention include acipimox, aluminum nicotinate, atorvastatin, cholestyramine resin, colestipol, polidexide, beclobrate bezafibrate, ciprofibrate, clinofibrate, clofibrate, clofibric acid, etofibrate, fenofibrate, fluvastatin, gemfibrozil, lovastatin, lysosomal acid lipase, icofibrate, niacin, pirifibrate, pravastatin sodium, ronifibrate, simfibrate, theofibrate, simvastatin, niceritrol, nicoclonate, nicomol oxiniacic acid, etiroxate, thyopropic acid, thyroxine, acifran, azacosterol, benfluorex, beta-benzalbutyramide, carnitine, chondroitin sulfate clomestrone, detaxtran, dextran sulfate sodium, 5, 8, 11, 14, 17-eicosapentaenoic acid, eritadenine, furazabol, meglutol, melinamide, mytatrienediol, ornithine, gamma-oryzanol, pantethine, pentaerythritol tetraacetate, alpha-phenylbutyramide, pirozadil, probucol, beta-sitosterol, sultosilic acid (piperazine salt), tiadenol, triparanol, xenbucin, and mixtures thereof.

Antidiabetics

Non-limiting examples of antidiabetics that may be used in the compositions of the present invention include biguanides such as buformin, metformin, and phenformin; hormones such as insulin; sulfonylurea derivatives such as acetohexamide, 1-butyl-3-metanilylurea, carbutamide, chlorpropamide, glibornuride, gliclazide, glimepiride, glipizide, gliquidone, glisoxepid, glyburide, glybuthiazole, glybuzole, glyhexamide, glymidine, glypinamide, phenbutamide, tolazamide, tolbutamide, tolcyclamide; HDL agonists; PPARγ agonists such as thiazolidinediones such as pioglitazone, rosiglitazone, and troglitazone; and others including acarbose, calcium mesoxalate, miglitol, and repaglinide.

Antiinflammatory Agents

Non-limiting examples of antiinflammatory agents that may be used in the compositions of the present invention include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin;

Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. One preferred antiinflammatory agent is aspirin.

Calcium Channel Blockers

Calcium channel blockers are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Non-limiting examples of calcium channel blockers that may be used in the compositions of the present invention include bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidpine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, and mixtures thereof.

CETP Inhibitors

A non-limiting example of a CETP inhibitor that may be used in the compositions of the present invention includes torcetrapib.

COX-2 Inhibitors

Non-limiting examples of COX-2 inhibitors that may be used in the compositions of the present invention include compounds according to the following: all of the compounds and substances beginning on page 8 of Winokur WO99/20110 as members of three distinct structural classes of selective COX-2 inhibitor compounds, and the compounds and substances which are selective COX-2 inhibitors in Nichtberger, U.S. Pat. No. 6,136,804, Oct. 24, 2000, entitled "Combination therapy for treating, preventing, or reducing the risks associated with acute coronary ischemic syndrome and related conditions", and the compounds and substances which are selective COX-2 inhibitors in Isakson et al, PCT application WO/09641645 published Dec. 27, 1996, filed as PCT/US 9509905 on Jun. 12, 1995, entitled "Combination of a Cyclooxygenase-2 Inhibitor and a Leukotriene B4 Receptor Antagonist for the Treatment of Inflammations." The meaning of COX-2 inhibitor in this invention shall include the compounds and substances referenced and incorporated into Winokur WO99/20110 by reference to art therein, the compounds and substances referenced and incorporated into Nichtberger, U.S. Pat. No. 6,136,804, Oct. 24, 2000, by reference to art therein, and the compounds and substances which are COX-2 inhibitors referenced and incorporated into Isakson et al, PCT application WO/09641645 published Dec. 27, 1996, filed as PCT/US 9509905 on Jun. 12, 1995, entitled "Combination of a Cyclooxygenase-2 Inhibitor and a Leukotriene B4 Receptor Antagonist for the Treatment of Inflammations." The meaning of COX-2 inhibitor in this invention also includes rofecoxib, and celecoxib, marketed as VIOXX and CELEBREX by Merck and Searle/Pfizer respectively. Rofecoxib is discussed in Winokur, WO99/20110 as compound 3, on p. 9. Celecoxib is discussed as SC-58635 in the same reference, and in T. Penning, Synthesis and biological evaluation of the 1,5-diarylpyrazole class of cyclooxygenase-2 inhibitors: identification of 4-[5-(4-methylphenyl)-3-(trifluoromethyl)-1H-pyrozol-1-yl]benzenesulfonami de (SC-58635, celecoxib)", J. Med. Chem. Apr. 25, 1997: 40(9): 1347-56. The meaning of COX-2 inhibitor in this invention also includes SC299 referred to as a fluorescent diaryloxazole. C. Lanzo et al, "Fluorescence quenching analysis of the association and dissociation of a diarylheterocycle to cyclooxygenasel-1 and cyclooxygenase-2: dynamic basis of cycloxygenase-2 selectivity", Biochemistry May 23, 2000, vol. 39(20):6228-34, and in J. Talley et al, "4,5-Diaryloxazole inhibitors of cyclooxygenase-2 (COX-2)", Med. Res. Rev. May 1999; 19(3): 199-208. The meaning of COX-2 inhibitor in this invention also includes valdecoxib, See, "4-[5-Methyl-3-phenylisoxazol-1-yl]benzenesulfonamide, Valdecoxib: A Potent and Selective Inhibitor of COX-2", J. Med. Chem. 2000, Vol. 43: 775-777, and parecoxib, sodium salt or parecoxib sodium, See, N-[[(5-methyl-3-phenylixoxazol-4yl)-phenyl]sulfonyl]propanimide, Sodium Salt, Parecoxib Sodium: A Potent and Selective Inhibitor of COX-2 for Parenteral Administration", J. Med. Chem. 2000, Vol. 43: 1661-1663. The meaning of COX-2 inhibitor in this invention also includes the substitution of the sulfonamide moiety as a suitable replacement for the methylsulfonyl moiety. See, J. Carter et al, Synthesis and activity of sulfonamide-substituted 4,5-diaryl thiazoles as selective cyclooxygenase-2 inhibitors." Bioorg. Med. Chem. Lett Apr. 19, 1999: Vol. 9(8): 1171-74, and compounds referenced in the article "Design and synthesis of sulfonyl-substituted 4,5-diarylthiazoles as selective cyclooxygenase-2 inhibitors", Bioorg. Med. Chem. Lett Apr. 19, 1999: Vol. 9(8): 1167-70. The meaning of this invention includes a COX-2 inhibitor, NS398 referenced in two articles: Attiga et al, "Inhibitors of Prostaglandin Synthesis Inhibit Human Prostate Tumor Cell Invasiveness and Reduce the Release of Matrix Metalloproteinases", 60 Cancer Research 4629-4637, Aug. 15, 2000, and in "The cyclooxygenase-2 inhibitor celecoxib induces apoptosis by blocking Akt activation in human prostate cancer cells independently of Bcl-2," Hsu et al, 275(15) J. Biol. Chem. 11397-11403 (2000). The meaning of COX-2 inhibitor in this invention includes the cyclo-oxygenase-2 selective compounds referenced in Mitchell et al, "Cyclo-oxygenase-2: pharmacology, physiology, biochemistry and relevance to NSAID therapy", Brit. J. of Pharmacology (1999) vol. 128: 1121-1132, see especially p. 1126. The meaning of COX-2 inhibitor in this invention includes so-called NO-NSAIDs or nitric oxide-releasing-NSAIDs referred to in L. Jackson et al, "COX-2 Selective Nonsteroidal Anti-Inflammatory Drugs: Do They Really Offer Any Advantages?", Drugs, June, 2000 vol. 59(6): 1207-1216 and the articles at footnotes 27, and 28. Also included in the meaning of COX-2 inhibitor in this invention includes any substance that selectively inhibits the COX-2 isoenzyme over the COX-1 isoenzyme in a ratio of greater than 10 to 1 and preferably in ratio of at least 40 to 1 as referenced in Winokur WO 99/20110, and has one substituent having both atoms with free electrons under traditional valence-shell-electron-pair-repulsion theory located on a cyclic ring (as in the sulfylamine portion of celecoxib), and a second substituent located on a different ring sufficiently far from said first substituent to have no significant electron interaction with the first substituent. The second substituent should have an electronegativity within such substituent greater than 0.5, or the second substituent should be an atom located on the periphery of the compound selected from the group of a halogen F, Cl, Br or I, or a group VI element, S or O. Thus for purposes of this last included meaning of a COX-2 inhibitor, one portion of the COX-2 inhibitor should be hydrophilic and the other portion lipophilic. Also included as a COX-2 inhibitor are compounds listed at page 553 in Pharmacotherapy: A Pathophysiologic Approach, Depiro et al (McGraw Hill 1999) including nabumetone and etodolac. Recognizing that there is overlap among the selective COX-2 inhibitors set out in this paragraph, the intent of the term COX-2 inhibitor is to comprehensively include all selective COX-2 inhibitors, selective in the sense of inhibiting COX-2 over COX-1. The inventors add to the class of COX-2 inhibitors useful in the invention the drug bearing the name etoricoxib referenced in the Wall Street Journal, Dec. 13, 2000, manufactured by Merck. See, also, Chauret et al., "In vitro metabolism considerations, including activity testing of metabolites, in the discovery and selection of the COX-2 inhibitor etoricoxib (MK-0663)," Bioorg. Med. Chem. Lett. 11(8): 1059-62 (Apr. 23, 2001). Another selective COX-2 inhibitor is DFU [5,5-dimethyl-3-(3-fluorophenyl)-4-(4-methylsulphonyl) phenyl-2 (5H)-furanone] referenced in Yergey et al, Drug Metab. Dispos. 29(5): 638-44 (May 2001). The inventors also include as a selective COX-2 inhibitor the flavonoid antioxidant silymarin, and an active ingredient in silymarin, silybinin, which demonstrated significant COX-2 inhibition relative to COX-1 inhibition. The silymarin also showed protection against depletion of glutathione peroxidase. Zhao et al, "Significant Inhibition by the Flavonoid Antioxidant Silymarin against 12-O-tetracecanoylphorbol 13-acetate-caused modulation of antioxidant and inflammatory enzymes, and cyclooxygenase 2 and interleukin-1 alpha expression in SENCAR mouse epidermis: implications in the prevention of stage I tumor promotion," Mol. Carcinog. December 1999, Vol 26(4):321-33 PMID 10569809. Silymarin has been used to treat liver diseases in Europe.

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

"Direct Thrombin Inhibitors"

Non limiting examples of direct thrombin inhibitors include hirudin, hirugen, hirulog, agatroban, PPACK, and thrombin aptamers.

Diuretics

Non-limiting examples of diuretics that may be used in the compositions of the present invention include althiazide, bendroflumethiazide, benzthiazide, buthiazide, chlorthalidone, cyclopenthiazide, cyclothiazide, epithiazide, ethiazide, fenquizone, indapamide, hydroflumethiazide, methyclothiazide, meticrane, metolazone, paraflutizide, polythiazide, quinethazone, teclothiazide, trichloromethiazide, chlormerodrin, meralluride, mercamphamide, mercaptomerin sodium, mercumatilin sodium, mercurous chloride, mersalyl, acefylline, 7-morpholinomethyl-theophylline, pamabrom, protheobromine, theobromine, canrenone, oleandrin, spironolactone, acetazolamide, ambuside, azosemide, bumetamide, butazolamide, clopamide, clrexolone, disufamide, ethoxzolamide, furosemide, mefruside, methazolamide, piretanide, torsemide, tripamide, xipamide, aminometradine, amisometradine, amanozine, amiloride, arbutin, chlorazanil, ethacrynic acid, etozolin, hydracarbazine, isosorbide, mannitol, metochalcone, muzolimine, perhexiline, ticrynafen, triamterene, urea, and mixtures thereof.

Endothelin Receptor Antagonists

A non-limiting example of an endothelin receptor antagonist that may be used in the compositions of the present invention is bosentan.

HMG-CoA Reductase Inhibitor (Statins)

HMG-CoA (3-hydroxy-3-methylglutaryl-coenzyme A) reductase is the microsomal enzyme that catalyzes the rate limiting reaction in cholesterol biosynthesis (HMG-CoA6Mevalonate). An HMG-CoA reductase inhibitor inhibits HMG-CoA reductase, and as a result inhibits the synthesis of cholesterol. A number of HMG-CoA reductase inhibitors has been used to treat individuals with hypercholesterolemia. More recently, HMG-CoA reductase inhibitors have been shown to be beneficial in the treatment of stroke (Endres M, et al., Proc Natl Acad Sci USA, 1998, 95:8880-5).

HMG-CoA reductase inhibitors useful for co-administration with the agents of the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985; 5,135,935; 5,356,896; 4,920,109; 5,286,895; 5,262,435; 5,260,332; 5,317,031; 5,283,256; 5,256,689; 5,182,298; 5,369,125; 5,302,604; 5,166,171; 5,202,327; 5,276,021; 5,196,440; 5,091,386; 5,091,378; 4,904,646; 5,385,932; 5,250,435; 5,132,312; 5,130,306; 5,116,870; 5,112,857; 5,102,911; 5,098,931; 5,081,136; 5,025,000; 5,021,453; 5,017,716; 5,001,144; 5,001,128; 4,997,837; 4,996,234; 4,994,494; 4,992,429; 4,970,231; 4,968,693; 4,963,538; 4,957,940; 4,950,675; 4,946,864; 4,946,860; 4,940,800; 4,940,727; 4,939,143; 4,929,620; 4,923,861; 4,906,657; 4,906,624 and 4,897,402, the disclosures of which patents are incorporated herein by reference.

Other non-limiting examples of HMG-CoA reductase inhibitors that may be used in the compositions of the present invention include mevastatin, pitavastatin, rosuvastatin, gemcabene, and probucol.

Inotropic Agents

Non-limiting examples of inotropic agents that may be used in the compositions of the present invention include acefylline, acetyldigitoxins, 2-amino-4-picoline, amrinone, benfurodil hemisuccinate, bucladesine, camphotamide, convallatoxin, cymarin, denopamine, deslanoside, digitalin, digitalis, digitoxin, digoxin, dobutamine, docarpamine, dopamine, dopexamine, enoximone, erythrophleine, fenalsomine, gitalin, gitoxin, glycocyamine, heptaminol, hydrastinine, ibopamine, lanatosides, loprinine, milrinone, nerifolin, oleandrin, ouabain, oxyfedrine, pimobendan, prenalterol, proscillaridin, resibufogenin, scillaren, scillarenin, strophanthin, sulmazole, theobromine, vesnarinone, xamoterol, and mixtures thereof.

"Renin Inhibitors"

Renin inhibitors are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Vasodilators

Non-limiting examples of vasodilators that may be used in the compositions of the present invention include bencyclane, cinnarizine, citicoline, cyclandelate, ciclonicate, diisopropylamine dichloroacetate, eburnamonine, fasudil, fenoxedil, flunarizine, ibudilast, ifenprodil, lomerixine, nafronyl, nicametate, nicergoline, nimodipine, papaverine, pentifylline, tinofedrine, vancamine, vinpocetine, viquidil, amotriphene, bendazol, benfurodil hemisuccinate, benziodarone, chloracizine, chromonar, clobenfurol, clonitrate, cloricromen, dilazep, dipyridamole, droprenilamine, efloxate, erythrityl tetranitrate, etafenone, fendiline, floredil, ganglefence, heart muscle extract, hexestrol bis(β-diethylaminoethyl ether), hexobendine, itramin tosylate khellin, lidoflazine, mannitol hexanitrate, medibazine, nitroglycerin, isosorbide mononitrate, isosorbide dinitrate, and other nitrates, pentaerythritol tetranitrate, pentrinitrol, perhexiline, pimethylline, prenylamine, propatyl nitrate, pyridofylline, trapidil, tricromyl, trimetazidine, trolnitrate phosphate, visnadine, aluminum nicotinate, bamethan, bencyclane, betahistine, bradykinin, brovincamine, bufeniode, buflomedil, butalamine, cetiedil, ciclonicate, cinepazide, cinnarizine, cyclandelate, diisopropylamine dichloroacetate, eledoisin, fenoxedil, flunazine, hepronicate, ifenprodil, iloprost, inositol niacinate, isoxsuprine, kallidin, kallikrein, moxisylyte, nafronyl, nicametate, nicergoline, nicofuranose, nicotinyl alcohol, nylidrin, pentifylline, pentoxifylline, piribedil, prostaglandin $E_1$, suloctidil, tolazoline, xanthinol niacinate, and mixtures thereof.

Vasopressors

Non-limiting examples of vasopressors that may be used in the compositions of the present invention include amezinium methyl sulfate, angiotensin amide, dimetofrine, dopamine, etifelmin, etilefrin, gepefrine, metaraminol, methoxamine, midodrine, norepinephrine, pholedrine, synephrine, and mixtures thereof.

AGE Crosslink Breakers (Advanced Glycosylation End-product Crosslink Breakers)

Non-limiting examples of AGE crosslink breakers that may be used in the compositions of the present invention include Alagebrium.

AGE Formation Inhibitors (Advanced Glycosylation End-product Formation Inhibitors)

Non-limiting examples of AGE formation inhibitors that may be used in the compositions of the present invention include Pimagedine.

Other Actives:

Non-limiting examples of other active ingredients that may be combined with these nebivolol compositions include, but are not limited to, the following representative classes of compounds, as well as their pharmaceutically acceptable salts, isomers, esters, ethers and other derivatives:

analgesics and anti-inflammatory agents, such as aloxiprin, auranofin, azapropazone, benorylate, capsaicin, celecoxib, diclofenac, diflunisal, etodolac, fenbufen, fenoprofen calcium, flurbiprofen, ibuprofen, indomethacin, ketoprofen, ketorolac, leflunomide, meclofenaminc acid, mefenamic acid, nabumetone, naproxen, oxaprozin, oxyphenbutazone, phenylbutazone, piroxicam, rofecoxib, sulindac, tetrahydrocannabinol, tramadol and tromethamine;

antihelminthics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-asthma agents, such as zileuton, zafirlukast, terbutaline sulfate, montelukast, and albuterol;

anti-bacterial agents, such as alatrofloxacin, azithromycin, baclofen, benzathine penicillin, cinoxacin, ciprofloxacin HCl, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifampicin, rifabutine, rifapentine, sparfloxacin, spiramycin, sulphabenzamide, sulphadoxine, sulphamerazine, ulphacetamide, sulphadiazine, sulphafurazole, sulphamethoxazole, sulphapyridine, tetracycline, trimethoprim, trovafloxacin, and vancomycin;

anti-viral agents, such as abacavir, amprenavir, delavirdine, efavirenz, indinavir, lamivudine, nelfinavir, nevirapine, ritonavir, saquinavir, and stavudine;

anti-depressants, such as amoxapine, bupropion, citalopram, clomipramine, fluoxetine HCl, maprotiline HCl, mianserin HCl, nortriptyline HCl, paroxetine HCl, sertraline HCl, trazodone HCl, trimipramine maleate, and venlafaxine HCl;

anti-epileptics, such as beclamide, carbamazepine, clonazepam, ethotoin, felbamate, fosphenyloin sodium, lamotrigine, methoin, methsuximide, methylphenobarbitone, oxcarbazepine, paramethadione, phenacemide, phenobarbitone, phenyloin, phensuximide, primidone, sulthiame, tiagabine HCl, topiramate, valproic acid, and vigabatrin;

anti-fungal agents, such as amphotericin, butenafine HCl, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, erbinafine HCl, terconazole, tioconazole and undecenoic acid;

anti-gout agents, such as allopurinol, probenecid and sulphinpyrazone;

anti-malarials, such as amodiaquine, chloroquine, chlorproguanil HCl, halofantrine HCl, mefloquine HCl, proguanil HCl, pyrimethamine and quinine sulfate;

anti-migraine agents, such as dihydroergotamine mesylate, ergotamine tartrate, frovatriptan, methysergide maleate, naratriptan HCl, pizotifen maleate, rizatriptan benzoate, sumatriptan succinate, and zolmitriptan;

anti-muscarinic agents, such as atropine, benzhexol HCl, biperiden, ethopropazine HCl, hyoscyamine, mepenzolate bromide, oxyphencyclimine HCl and tropicamide;

anti-neoplastic agents and immunosuppressants, such as aminoglutethimide, amsacrine, azathioprine, bicalutamide, bisantrene, busulfan, camptothecin, capecitabine, chlorambucil, cyclosporin, dacarbazine, ellipticine, estramustine, etoposide, irinotecan, lomustine, melphalan, mercaptopurine, methotrexate, mitomycin, mitotane, mitoxantrone, mofetil mycophenolate, nilutamide, paclitaxel, procarbazine HCl, sirolimus, tacrolimus, tamoxifen citrate, teniposide, testolactone, topotecan HCl, and toremifene citrate;

anti-protozoal agents, such as atovaquone, benznidazole, clioquinol, decoquinate, diiodohydroxyquinoline, diloxanide furoate, dinitolmide, furazolidone, metronidazole, nimorazole, nitrofurazone, ornidazole and tinidazole;

anti-psychotics, such as aripiprazole, clozapine, ziprasidone, haloperidol, molindone, loxapine, thioridazine, molindone, thiothixene, pimozide, fluphenazine, risperidone mesoridazine, quetiapine, trifluoperazine, chlorprothixene, chlorpromazine, perphenazine, trifluopromazine, olanzapine;

anti-thyroid agents, such as carbimazole, paracalcitol, and propylthiouracil;

anti-tussives, such as benzonatate;

anxiolytics, sedatives, hypnotics and neuroleptics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, diazepam, droperidol, ethinamate, flunanisone, flunitrazepam, triflupromazine, flupenthixol decanoate, fluphenthixol decanoate, flurazepam, gabapentin, haloperidol, lorazepam, lonnetazepam, medazepam, meprobamate, mesoridazine, methaqualone, methylphenidate, midazolam, molindone, nitrazepam, olanzapine, oxazepam, pentobarbitone, perphenazine pimozide, prochlorperazine, pseudoephedrine, quetiapine, risperidone, sertindole, sulpiride, temazepam, thioridazine, triazolam, zolpidem, and zopiclone;

corticosteroids, such as beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone and triamcinolone;

anti-parkinsonian agents, such as apomorphine, bromocriptine mesylate, lysuride maleate, pramipexole, ropinirole HCl, and tolcapone;

gastro-intestinal agents, such as bisacodyl, cimetidine, cisapride, diphenoxylate HCl, domperidone, famotidine, lanosprazole, loperamide, mesalazine, nizatidine, omeprazole, ondansetron HCL, rabeprazole sodium, ranitidine HCl and sulphasalazine;

keratolytics, such as acetretin, calciprotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, fenofibrate, fluvastatin, gemfibrozil, pravastatin, probucol, and simvastatin;

muscle relaxants, such as dantrolene sodium and tizanidine HCl;

nutritional agents, such as calcitriol, carotenes, dihydrotachysterol, essential fatty acids, non-essential fatty acids, phytonadiol, vitamin A, vitamin B.sub.2, vitamin D, vitamin E and vitamin K;

opioid analgesics, such as codeine, dextropropoxyphene, diamorphine, dihydrocodeine, fentanyl, meptazinol, methadone, morphine, nalbuphine and pentazocine;

sex hormones, such as clomiphene citrate, cortisone acetate, danazol, dehydroepiandrosterone, ethynyl estradiol, finasteride, fludrocortisone, fluoxymesterone, medroxyprogesterone acetate, megestrol acetate, mestranol, methyltestosterone, norethisterone, norgestrel, oestradiol, conjugated estrogens, progesterone, rimexolone, stanozolol, stilbestrol, testosterone and tibolone;

stimulants, such as amphetamine, dexamphetamine, dexfenfluramine, fenfluramine and mazindol;

drugs for rheumatoid arthritis such as methotrexate, auranofin, aurothioglucose and gold sodium thiomalate;

drugs for osteoporosis such as alendronate and raloxifene;

local anesthetics;

anti-herpes drugs such as acyclovir, valacyclovir and famcyclovir;

anti-emetics such as ondansetron and granisetron;

Further examples of other active agents which may be suitable for this invention include, without limitation: abecarnil, acamprostate, acavir, acebutolol, aceclofenac, acemetacin, acetaminophen, acetaminosalol, acetanilide, acetohexamide, acetophenazine maleate, acetophenazine, acetoxolone, acetoxypregnenolone, acetretin, acrisorcin, acrivastine, acyclovir, adinazolam, adiphenine hydrochloride, adrafinil, adrenolone, agatroban, ahnitrine, akatinol, alatrofloxacin, albendazole, albuterol, aldioxa, alendronate, alfentanil, alibendol, alitretinoin, allopurinol, allylamines, allylestrenol, alminoprofen, almotriptan, alosetron, aloxiprin, alprazolam, alprenolol, amantadine, ambucetamide, amidephrine, amidinomycin, amiloride, aminoarylcarboxylic acid derivatives, aminoglutethimide, aminoglycosides, aminopentamide, aminopromazine, a minorex, amiodarone, amiphenazole, amiprilose, amisulpride, amitriptyline, amlexanox, amlodipine, amodiaquine, amosulalol, amotriphene, amoxapine, amoxicillin, amphecloral, amphetamine, amphomycin, amphotericin, ampicillin, ampiroxicam, amprenavir, amrinone, amsacrine, amyl nitrate, amylobarbitone, anagestone acetate, anastrozole, andinocillin, androstenediol, androstenediol-17-acetate, androstenediol-17-benzoate, androstenediol-3-acetate, androstenediol-3-acetate-17-benzoate, androstenedione, androsterone acetate, androsterone benzoate, androsterone propionate, androsterone, angiotensin, anidulatungin, aniracetam, apazone, apicycline, apoatropine, apomorphine, apraclonidine, aprepitant, aprotinin, arbaprostil, ardeparin, aripiprazole, arnikacin, arotinolol, arstiinol, arylacetic acid derivatives, arylalkylamines, arylbutyric acid derivatives, arylcarboxylic acids, arylpiperazines, arylpropionic acid derivatives, aspirin, astemizole, atenolol, atomoxetine, atorvastatin, atovaquone, atropine, auranofn, azapropazone, azathioprine, azelastine, azetazolamide, azithromycin, baclofen, bambuterol, bamethan, barbitone, barnidipine, basalazide, beclamide, beclobrate, befimolol, bemegride, benazepril, bencyclane, bendazac, bendazol, bendroflumethiazide, benethamine penicillin, benexate hydrochloride, benfurodil hemisuccinate, benidipine, benorylate, bentazepam, benzhexol, benziodarone, benznidazole, benzoctamine, benzodiazepine derivatives, benzodiazepine, benzonatate, benzphetamine, benzylmorphine, beperiden, bephenium hydroxynaphthoate, bepridil, betahistine, betamethasone, betaxolol, bevantolol, bevonium methyl sulfate, bexarotene, bezadoxifine, bezafibrate, bialamicol, biapenem, bicalutamide, bietamiverine, bifonazole, binedaline, binifibrate, biricodar, bisacodyl, bisantrene, bisoprolol, bitolterol, bopindolol, boswellic acid, bradykinin, bretylium, bromazepam, bromocriptine, bromperidol, brotizolam, brovincamine, buciclate, bucloxic acid, bucumolol, budralazine, buieniode, bufetolol, buflomedil, bufuralol, bumetamide, bunitrolol, bupranolol, buprenorphine, buproprion, buspirone, busulfan, butalamine, butarphenol, butaverine, butenafine, butenatme, butidrine hydrochloride, butobarbitone, butoconazole nitrate, butoconazole, butofilol, butorphenol, butropium bromide, cabergoline, calcifediol, calcipotriene, calcitriol, caldibine, cambendazole, camioxirole, camostat, camposterol, camptothecin, candesartan, candoxatril, capecitabine, caprate, capsaicin, captopril, carazolol, carbacephems, carbamates, carbamezepine, carbapenems, carbarsone, carbatrol, carbenoxolone, carbimazole, carbromal, carbuterol, carisoprodol, carotenes, caroverine, carteolol, carvedilol, cefaclor, cefazolin, cefbuperazone, cefepime, cefoselis, ceftibuten, celcoxib, celecoxib, celiprolol, cephaeline, cephalosporin C, cephalosporins, cephamycins, cerivastatin, certoparin, cetamolol, cetiedil, cetirizine, cetraxate, chloracizine, chlorambucil, chlorbetamide, chlordantoin, chlordiazepoxide, chlormadinone acetate, chlormethiazole, chloroquine, chlorothiazide, chlorpheniramine, chlorphenoxamide, chlorphentermine, chlorproguanil, chlorpromazine, chlorpropamide, chlorprothixene, chlortetracycline, chlorthalidone, cholecalciferol, chromonar, ciclesonide, ciclonicate, cidofivir, ciglitazone, cilansetron, cilostazol, cimetidine, cimetropium bromide, cinepazet maleate, cinnamedrine, cinnarizine, cinolazepam, cinoxacin, ciprofibrate, ciprofloxacin, cisapride, cisplatin, citalopram, citicoline, clarithromycin, clebopride, clemastine, clenbuterol, clidanac, clinofibrate, clioquinol, clobazam, clobenfurol, clobenzorex, clofazimine, clofibrate, clofibric acid, cloforex, clomipramine, clonazepam, clonidine, clonitrate, clopidogrel, clopirac indomethacin, cloranolol, cloricromen, clorprenaline, clortermine, clotiazepam, clotrimazole, cloxacillin, clozapine, cmepazide, codeine methyl bromide, codeine phosphate, codeine sulfate, codeine, colloidal bismuth subcitrate, cromafiban, cromolyn, cropropamide, crotethamide, curcumin, cyclandelate, cyclarbamate, cyclazocine, cyclexedrine, cyclizine, cyclobenzaprine, cyclodrine, cyclonium iodide, cyclopentamine, cyclosporin, cypionate, cyproheptadine, cyproterone acetate, cytarabine, dacarbazine, dalfopristine, dantrolene sodium, dapiprazole, darodipine, decanoate, decitabine, decoquinate, dehydroemetine, delavirdine, del aviridine, demeclo cycline, denopamine, deramciclone, descitalopram, desipramine, desloratadine, 3-ketodesogeskel, desomorphine, desoxymethasone, detomidine, dexamphetamine, dexanabinol, dexchlorpheniramine, dexfenfluramine, dexmethylphenidate, dexrazoxane, dextroamphetamine sulfate, dextroamphetamine, dextropropoxyphene, DHEA, diacetate, diamorphine, diazemine, diazepam, diaziquinone, diazoxide, dibromopropamidine, dichlorophen, diclofenac, dicoumarol, didanosine, dideoxyadenosine, diethylpropion, difemerine, difenamizole, diflunisal, digitoxin, digoxin, dihidroergotamine, dihydrocodeine, diLydrocodeinone enol acetate, dihydroergotamine mesylate, dihydroergotamine, dihydrogesterone, dihydromorphine, dihydropyridine derivatives, dihydrostreptomycin, dihydrotachysterol, dihydroxyaluminum acetylsalicylate, diiodohydroxyquinoline, diisopromine, dilazep, dilevalol, dilitazem, diloxanide furoate, diloxanide, diltiazem, dimefline, dimenhydrinate, dimethisterone, dimetotrine, dimorpholamine, dinitolmide, dioxaphetyl butyrate, dioxethedrine, diphemethoxidine, diphenhydramine, diphenoxylate, diphetarsone, dipivefrin, diponium bromide, dipyridamole, dirithromycin, disopyramide, divalproex sodium, dofetilide, domperidone, donezepil, dopexamine, dopradil, dosmalfate, doxapram, doxazosin, doxefazepam, doxepin, doxycycline, drofenine, dromostanolone propionate, dromostanolone, dronabinol, droperidol, droprenilamine, d-threomethylphenidate, duloxetine, ebrotidine, eburnamonine, ecabet, ecenofloxacin, econazole nitrate, edavarone, edoxudine, efavirenz, effivarenz, efloxate, eledoisin, eletriptan, elgodipine, ellipticine, emepronium bromide, emetine, enalapril, enanthate, encainide, enlopitat, enoximone, enprostil, entacapone, epanolol, ephedrine, epinastine, epinephrine, epirubicin, eplerenone, eposartan, ergocalciferol, ergoloid mesylates, ergotamine, ertapenum, erythromycin, erytlirityl tetranitrate, esaprazole, escitalopram, esmolol, esomeprazole, esonarimod, estazolam, estradiol benzoate, estramustine, eskiol succinate, estrone acetate, estrone sulfate, etafedrine, etafenone, ethacrynic acid, ethamivan, ethinamate, ethinyleskadiol 3-acetate, ethinyleskadiol 3-benzoate, ethinylestradiol, ethionamide, ethisterone (17a-ethinyltestosterone), ethopropazine, ethotoin, ethoxyphenamine, ethylestrenol, ethylmorphine, ethylnorepinephrine, ethynodiol diacetate, etodolac, etofibrate, etoposide, etoricoxib, etretinate, everolimus, exalamide, examestane, examorelin, ezemitibe, falecalcitriol, famciclovir, famotidine, fantofarone, farapenum, farglitazar, fasudil, felbamate, felodipine, fenalamide, fenbuLen, fenbutrazate, fendiline, fenfluramine, fenoldopam, fenoprofen, fenoterol, fenoverine, fenoxazoline, fenoxedil, fenpiprane, fenproporex, fenspiride, fentanyl, fexofenadine, flavoxate, flecainide, flopropione, floredil, floxuridine, fluconazole, flucytosine, fludarabine, fludiazpam, fludrocortisone, flulenamic acid, flunanisone, flunarizine, flunisolide, flunitrazepam, fluocortolone, fluoxetine, flupenthixol decanoate, fluphenazine decanoate, fluphenazine enanthate, fluphenazine, fluproquazone, flurazepam, flurbiprofen, flurogestone acetate, fluticasone propionate, fluvastatin, fluvoxamine, fominoben, formoterol, foscarnet, foscarnet, fosinopril, fosphenyloin, frovatirptan, fudosteine, fumagillin, furazolidone, furazolidone, furfurylmethyl amphetamine, furosemide, gabapentin, gabexate, gaboxadol, galanthamine, gallopamil, gammaparin, gancyclovir, ganglefene, gefarnate, gemcitabine, gemfibrozil, gepirone, gestadene, ghrelin, glatiramer, glaucarubin, glibenclamide, gliclazide, glimepiride, glipizide, gluconic acid, glutamicacid, glyburide, glyceryl trinitrate, glymepiride, granisetron, grepafloxacin, griseofulvin, guaiazulene, guanabenz, guanfacine, halofankine, haloperidol decanoate, haloperidol, haloxazolam, hepronicate, heptanoate, hexobendine, hexoprenaline, hydramitrazine, hydrazides, hydro chlorothi azide, hydrocodone, hydrocortisone, hydromorphone, hydroxyamphetamine, hydroxymethylprogesterone acetate, hydroxymethylprogesterone, hydroxyprogesterone acetate, hydroxyprogesterone caproate, hydroxyprogesterone, hymecromone, hyoscyamine, ibopamine, ibudilast, ibutenac, ibuprofen, ibutilide, idoxuridine, ifenprodil, igmesine, iloprost, imatinib, imidapril, imidazoles, imipenem, imipramine, imolamine, incadronic acid pergolide, indanazoline, indenolol, indinavir, indomethacin, indoramin, inosinepranobex, inositol niacinate, iodoquinol, ipidracine, iproniazid, irbesartan, irinotecan, irsogladine, isobutyrate, isocaprate esters, isoetharine, isomethepene, isoproterenol, isosorbide dinitrate, isosorbide mononitrate, isosorbide dinitrate, isoxsuprine, isradipine, itasetron, itraconazole, itramintosylate, ivermectin, kallidin, kallikrein, kanamycin, ketamine, ketoconazole, ketoprofen, ketorolac, ketotifen, labetalol, lafutidine, lamifiban, lamivudine, lamotrigine, lanatoside c, lansoprazole, lasofoxifene, leflunomide, leminoprazole, lercanadipine, lesopitron, letrozole, leucovorin, levalbuterol, levallorphan, levetiracetam, levetriacetam, levobunolol, levodopa, levofloxacin, levophacetoperane, levorphanol, lidocaine, lidoflazine, lifibrol, limaprost, linezolid, lintitript, liranaftate, lisinopril, lisuride, lobeline, lobucavir, lodoxamide, lomefloxacin, lomerizine, lomustine, loperamide, lopinavir, loprazolam, loracarbef, loratadine, lorazepam, lorefloxacin, lormetazepam, losartan, lovasatain, lovastatin, loxapine succinate, loxapine, 1-threo methylphenidate, lumiracoxib, lysine acetylsalicylate, lysozyme, lysuride, mabuterol, mafenide, magnesium acetylsalicylate, malgramostin, mannitol hexanitrate, maprotiline, mazindol, mebendazole, meclizine, meclofenamic acid, mecloxaminepentapiperide, medazepam, medibazine, medigoxin, medrogestone, medroxyprogesterone acetate, mefenamic acid, mefenorex, mefloquin, mefloquine, megestrol acetate, melengestrol acetate, melphalan, mematine, mepenzolate bromide, meperidine, mephenoxalone, mephentermine, mepindolol, mepixanox, meprobamate, meptazinol, mercaptopurine, merropenum, mesalamine, mesalazine, mesoridazine besylate, mesoridazine, metaclazepam, metamfepramone, metampicillin, metaproterenol, metaraminol, methacycline, methadone hydrochloride, methadone, methamphetamine, methaqualone, methamphetamine, methoin, methotrexate, methoxamine, methsuximide, methylhexaneamine, methylphenidate d-threo-methylphenidate, methylphenidate, methylphenobarbitone, methylprednisolone, methysergide, metiazinic acid, metizoline, metoclopramide, metolazone, metoprolol, metoxalone, metripranolol, metronidazole, mexiletine, mexilitene, metaxalone, mianserin, mibefradil, miconazole, midazolam, midodrine, miglitol, milnacipran, milrinone, minoxidil, mirtazapine, misoprostol, mitomycin, mitotane, mitoxantrone, mizolastine, modafinil, mofebutazone, mofetil, molindone hydrochloride, molindone, molsidomine, monatepil, montelukast, monteplase, moprolol, moricizine, morphine hydrochloride, morphine sulfate, morphine, morpholine salicylate, mosapramine, moxifloxacin, moxisylvyte, moxonidine, mycophenolate, nabumetone, nadolol, nadoxolol, nadroparin, nafamostat, nafronyl, naftopidil, nalbuphine, nalidixic acid, nalmefene, nalorphine, naloxone, naltrexone, nandrolone benzoate, nandrolone cyclohexanecarboxylate, nandrolone cyclohexane-propionate, nandrolone decanoate, nandrolone furylpropionate, nandrolone phenpropionate, naphazoline, naproxen, naratriptan, natamycin, nateglinide, nebivalol, nedocromil, nefazodone, nefopam, nelfinavir, nemonapride, neomycin undecylenate, neomycin, neokofin, nesiritide, n-ethylamphetamine, nevibulol, nevirapine, nexopamil, nicametate, nicardipine, nicergoline, nicofibrate, nicofuranose, nicomorphine, nicorandil, nicotinyl alcohol, nicoumalone, nifedipine, nifenalol, nikethamide, nilutamide, nilvadipine, nimodipine, nimorazole, nipradilol, nisoldipine, nitisonone, nitrazepam, nitrofurantoin, nitrofurazone, nitroglycerin, nizatidine, norastemizole, norepinephrine, norethynodrel, norfenefrine, norfloxacin, norgestimate, norgeskel, norgestrienone, normethadone, normethisterone, normorphine, norpseudoophedrine, nortriptyline, novantrone, nylidrin, nystatin, octamylamine, octodrine, octopamine, ofloxacin, olanzapine, olanzapine, olapatadine, olmesartan, olopatidine, olsalazine, omapatrilat, omeprazole, ondasetron, opium, oprevelkin, orlistat, omidazole, omoprostil, oseltamivir, oxaliplatin, oxamniquine, oxandrolone, oxantel embonate, oxaprozin, oxatomide pemirolast, oxatomide, oxazopam, oxcarbazepine, oxfendazole, oxiconazole, oxiracetam, oxolinicacid, oxprenol, oxycodone, oxyfedrine, oxymetazoline, oxymorphone, oxyphenbutazone, oxyphencyclimine, oxyprenolol, ozagrel, paclitaxel, palonosetron, pantoprazole, papaverine, paracalcitol, paramethadione, parecoxib, pariprazole, paromomycin, paroxetine, parsalmide, pazinaclone, pemoline, penbutolol, penciclovir, penicillin G benzathine, penicillin G procaine, penicillin V, penicillins, pentaerythritol tetranitrate, pentaerythritol tetranitrate, pentapiperide, pentazocine, pentifylline, pentigetide, pentobarbitone, pentorex, pentoxifylline, pentrinitrol, perbuterol, perenzepine, pergolide, perhexiline, perindopril erbumine, perosone, perphenazine pimozide, perphenazine, phanquinone, phenacemide, phenacetin, phenazopyridine, phencarbamide, phendimetrazine, phenelzine, phenindione, phenmetrazine, phenobarbitone, phenoperidine, phenothiazines, phenoxybenzamine, phensuximide, phentermine, phentolamine, phenylsalicylate, phenylacetate, phenylbutazone, phenylephrinehydrochloride, phenylpropanolamine hydrochloride, phenylpropanolaminehydrochloride, phenylpropyl-methylamine, phenyloin, phloroglucinol, pholedrine, physostigwine salicylate, physostigmine, phytonadiol, phytosterols, piapenum, picilorex, piclamilast, picrotoxin, picumast, pifamine, pilsicainide, pimagedine, pimeclone, pimecrolimus, pimethylline, pimozide, pinaverium bromide, pindolol, pioglitazone, piperacillin, piperazine estrone sulfate, piperazine derivatives, piperilate, piracetam, pirbuterol, pirenzepine, piribedil, pirifibrate, piroxicam, pitavastatin, pizotyline, plaunotol, polaprezinc, polybenzarsol, polyestrol phosphate, practolol, pralnacasan, pramipexole, pranlukast, pravastatin, prazepam, praziquantel, prazosin, pregabalin, prenalterol, prenylamine, pridinol, prifinium bromide, primidone, primipramine, probenecid, probucol, procainamide, procarbazine, procaterol, prochlorperazine, proguanil, pronethalol, propafenone, propamidine, propatyl nitrate, propentoffyline, propionate, propiram, propoxyphene, propranolol, propylhexedrine, propylthiouracil, protokylol, protriptyline, proxazole, pseudoephedrine, purines, pyrantel embonate, pyrazoles, pyrazolones, pyridofylline, pyrimethamine, pyrimidines, pyrrolidones, quazepam, quetiapine, quetuapine, quinagolide, quinapril, quinestrol, quinfamide, quinidine, quinine sulfate, quinolones, quinupritin, rabalzotan, rabeprazole sodium, rabeprazole, racefimine, ramahroban, ramipril, ranitidine, ranolazine, ransoprazole, rasagiline, rebamipide, refludan, repaglinide, repinotan, repirinast, reproterol, reserpine, retinoids, ribavirin, rifabutine, rifampicin, rifapentine, rilmenidine, riluzole, rimantadine, rimiterol, rioprostil, risperidone, ritanovir, ritapentine, ritipenem, ritodrine, ritonavir, rivastigmine, rizatriptan, rociverine, rofecoxib, rohypnol, rolipram, romoxipride, ronifibrate, ropinirole, ropivacaine, rosaprostol, rosiglitazone, rosuvastatin, rotinolol, rotraxate, roxatidine acetate, roxindole, rubitecan, salacetamide, salicin, salicylamide, salicylic acid derivatives, salmeterol, saquinavir, saquinavir, scopolamine, secnidazole, selegiline, semotiadil, sertindole, sertraline, sibutramine, sildenafil, simBibrate, simvastatin, siramesine, sirolimus, sitaxsentan, sofalcone, somotiadil, sorivudine, sotalol, soterenol, sparfloxacin, spasmolytol, spectinomycin, spiramycin, spizofurone, stavudine, streptomycin, succinylsulfathiazole, sucralfate, sufentanil, sulconazole nitrate, sulfacetamide, sulfadiazine, sulfaloxicacid, sulfarside, sulfinalol, sulindac, suloctidil, sulphabenzamide, sulphacetamide, sulphadiazine, sulphadoxine, sulphafurazole, sulphamerazine, sulphamethoxazole, sulphapyridine, sulphasalazine, sulphinpyrazone, sulpiride, sulthiame, sultopride, sulbroponium, sumanirole, sumahriptan, sunepihon, superoxide dismutase, suplatast, suramin sodium, synephrine, tacrine, tacrolimus, tacrolimus, tadalafil, talinolol, talipexole, tamoxifen, tainsulosin, targretin, tazanolast, tazarotene, tazobactum, tecastimezole, teclozan, tedisamil, tegaserod, telenzepine, telmisartan, temazepam, teniposide, teprenone, terazosin, terbenafine, terbinafine, terbutaline sulfate, terbutaline, terconazole, terfenadine, terodiline, terofenamate, tertatolol, testolactone, 4-dihydrotestosterone, tetracyclics, tetracycline, tetrahydrocannabinol, tehrahydrozoline, thalidomide, theofibrate, thiabendazole, thiazinecarboxamides, thiocarbamates, thiocarbamizine, thiocarbarsone, thioridazine, thiothixene, tiagabine, tiamenidine, tianeptine, tiaprofenic acid, tiaramide, ticlopidine, tigloidine, tilisolol, timolol, tinidazole, tinofedrine, tinzaparin, tioconazole, tipranavir, tirapazamine, tirofiban, tiropramide, titanicene, tizanadine, tizanidine, tizinadine, tocainide, tolazamide, tolazoline, tolbutamide, tolcapone, tolciclate, tolfenamic acid, toliprolol, tolteridine, tolterodine, tonaberstat, topiramate, topotecan, torasemide, toremifene cibrate, toremifene, tosufloxacin, tramadol, tramazoline, trandolapril, tranilast, tranylcypromine, trapidil, traxanox, trazodone, tretoquinol, triacetin, triamcinolone, triampterine, triamterene, triazolam, trifluoperazine hydrochloride, trifluoperazine, triflupromazine, trihexyphenidyl, trimazosin, trimebutine, trimetazidine, trimethoprim, trimgestone, trimipramine, trimoprostil, trithiozine, troglitazone, trolnibrate phosphate, tromethamine, tropicamide, trovafloxacin, troxipide, tuaminoheptane, tulobuterol, tymazoline, tyramine, undecanoate, undecanoic acid, urinastatin, valacyclovir, valdecoxib, valerate, valganciclovir, valproic acid, valsartan, vancomycin, vardenafil, venlafaxine, venorelbine, verapamil, verapimil, vidarabine, vigabakin, vincamine, vinpocetine, viomycin, viquidil, visnadine, vitamin a derivatives, vitamin a, vitamin $b_2$, vitamin d, vitamin e, vitamin k, voglibose, voriconazole, xaliproden, xamoterol, xanthinol niacinate, xenytropium bromide, xibenolol, ximelagatran, xylometazoline, yohimbine, zacopride, zafirlukast, zalcitabine, zaleplon, zanamivir, zatebradine, ziconotide, zidovudine, zileuton, zimeldine, zinc propionate, ziprasidone, zolimidine, zolmitriptan, zolpidem, zonisamide, zopiclone, and mixtures thereof.

Formulation

The nebivolol compositions of the present invention may be administered by various means, depending on their intended use, as is well known in the art. For example, if compositions of the present invention are to be administered orally, they may be formulated as tablets, capsules, granules, powders, suspensions or syrups. Alternatively, formulations of the present invention may be administered parenterally as injections (intravenous, intramuscular or subcutaneous), drop infusion preparations or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound(s). A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Pharmaceutical formulations may also be extended or delayed release formulations where the active agents are released over an extended period of time.

Dosages

Administration of the compositions of the present invention will be in an amount sufficient to achieve a therapeutic effect as recognized by one of ordinary skill in the art.

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the steroidal anti inflammatory drug) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

In general, the doses of an active agent will be chosen by a physician based on the age, physical condition, weight and other factors known in the medical arts.

Efficacy of Treatment

The efficacy of treatment with the subject compositions may be determined in a number of fashions known to those of skill in the art.

In one exemplary method, the median rate of decrease in inflammation for treatment with a subject composition may be compared to other forms of treatment with the particular cardiovascular agent contained in the subject composition, or with other cardiovascular agents. The decrease in inflammation for treatment with a subject composition as compared to treatment with another method may be 10, 25, 50, 75, 100, 150, 200, 300, 400% greater or even more. The period of time for observing any such decrease may be about 1, 3, 5, 10, 15, 30, 60 or 90 or more hours. The comparison may be made against treatment with the particular cardiovascular agent contained in the subject composition, or with other cardiovascular agents, or administration of the same or different agents by a different method, or administration as part of a different drug delivery device than a subject composition. The comparison may be made against the same or a different effective dosage of the various agents.

Alternatively, a comparison of the different treatment regimens described above may be based on the effectiveness of the treatment, using standard indices known to those of skill in the art. One method of treatment may be 10%, 20%, 30%, 50%, 75%, 100%, 150%, 200%, 300% more effective, than another method.

Alternatively, the different treatment regimens may be analyzed by comparing the therapeutic index for each of them, with treatment with a subject composition as compared to another regimen having a therapeutic index two, three, five or seven times that of, or even one, two, three or more orders of magnitude greater than, treatment with another method using the same or different cardiovascular agents.

Kits

This invention also provides kits for conveniently and effectively implementing the methods of this invention. Such kits comprise any subject composition, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means include instructions, packaging, and dispensing means, and combinations thereof. Kit components may be packaged for either manual or partially or wholly automated practice of the foregoing methods. In other embodiments involving kits, this invention contemplates a kit including compositions of the present invention, and optionally instructions for their use.

EXEMPLIFICATION

Example 1

Measurements of NO Release from Human Endothelium

All measurements presented were recorded in vitro using a sensitive porphyrinic probe, as previously described. Malinski T, Taha Z., *Nature*. 1992; 358:676-678; Malinski T, Czuchajowski L., *Methods in Nitric Oxide Research*. 1996: 319-339. NO release was measured directly from HUVEC. HUVEC cells from Black and White donors were grown in Ham's F12K medium with 2 mM L-glutamine adjusted to contain 1.5 g/L sodium bicarbonate and supplemented with 0.1 mg/ml heparin and 0.03-0.05 mg/ml endothelial cell growth supplement (ECGS)+10% fetal bovine serum. The HUVEC cells were kept in an atmosphere of elevated CO2 concentration (5%). Nebivolol was obtained from Mylan Laboratories (Morgantown, W. Va.).

All measurements of endothelial NO release were conducted in Hank's balance solution at 37° C. Cell wells were transferred to a Faraday cage and a porphyrinic sensor (diameter 0.5 mm) was positioned at a distance of 5±2 µm from the surface of the endothelial cells using an inverted microscope (Leica Microsystems, Wetzlar, Germany) and a computer-assisted micromanipulator. The sensor operated with a three-electrode system: nanosensor (working electrode), saturated calomel electrode (reference electrode) and platinum wire (counter electrode, 0.5 mm diameter). The three electrodes were connected to a potentiostat/galvanostat PAR273. The baseline was stabilized after about 20 seconds. The test compounds were injected with a nanoinjector onto the surface of the cells following solubilization in buffer. Cells were incubated with the test compounds for a 24-hour period. The compounds were then washed out of the system before being immediately reintroduced in order to evaluate the consequences of chronic treatment on NO release from the cells. For additive experiments, cells were incubated with ACE inhibitor for 24 hours, the inhibitor was washed out of the system, nebivolol was added and the NO release measured. The current proportional to the NO concentration was measured with the sensor, which operated in amperometric mode at a constant potential of 0.63V. Data were acquired with the use of an IBM computer with custom software and amperograms (current vs. time curves) were recorded with a Guniry FAS1 Femtostat (Warminster, Pa.). Maximum release of NO was produced using a calcium agonist (1 µM). By increasing cytoplasmic levels of calcium, the ion can bind to calmodulin. The Ca2+-calmodulin complex is a cofactor for endothelial NO synthase, along with FAD, FMN, Heme and BH4.

Nanosensors were prepared from carbon fibers. The size of the tip of carbon fiber was reduced from 61 µm to less than 1 µm by temperature controlled burning. The sensors were sensitized to NO by deposition of electrically conductive polymeric porphyrin and covered with a thin layer of Nafion. The porphyrinic microsensor has a response time of 0.1 ms at a micromolar NO concentration and 10 ms at the detection limit of 1 nM.

The nanosensor for NO was calibrated using saturated solution (concentration 1.82 mM verified with the coulometric method). Linear calibration curves were constructed for each sensor from 5×10-9 to 3×10$^{-6}$M NO before and after measurements of cell activity. The concentration-dependent effects of nebivolol and certain ACE-inhibitors on NO releasing capacity were tested using a calcium ionophore (A23187) that stimulates NO release, independently of G-protein-coupled receptors. The data were presented as the mean±SEM for each of the triplicate measurements. The data (calculation and plotting) were transferred to Microcal Origin Software (OriginLab Corp., Northampton, Mass.).

The HUVEC preparation is stable over the course of these experiments with the cells remaining viable in culture for >24 hours. Under non-stimulating conditions, basal levels of NO release are very low (<30 nM). Measurement of NO release as a function of treatment was conducted in individual endothelial cells. Multiple measurements of NO release can be conducted on single cells following a brief refractory period. For robust statistical analysis, separate cells were used for each concentration and type of drug used in these analyses.

In FIG. 1, the extent of NO release from Black and White donors was measured after chronic treatment with the ACE inhibitor, ramiprilat, followed by treatment with nebivolol (1 µM). At concentrations of 1, 5, and 10 µM ramiprilat, there were modest but significant effects in the ability of nebivolol to increase NO release from Black and White donor endothelial cells. The magnitude of the increase is greater in endothelial cells from Black donors.

Figure 3:
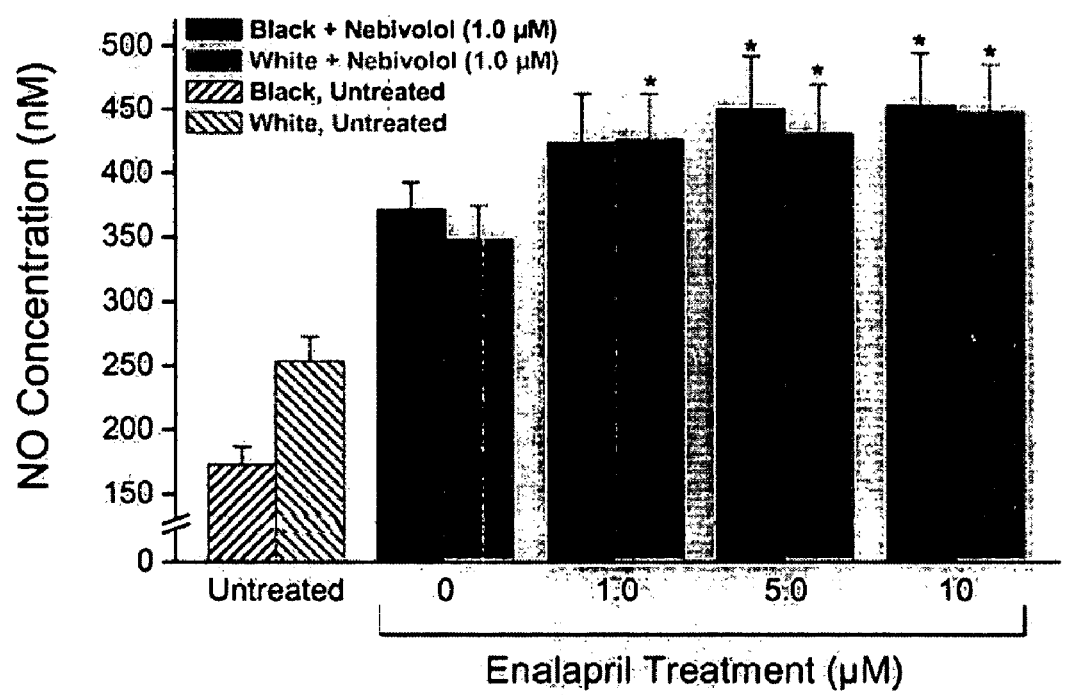
FIG. 3 depicts comparison of NO release from Black and White donor endothelial cells after chronic treatment with enalapril followed by treatment with nebivolol (1 μM).
Figure 4:
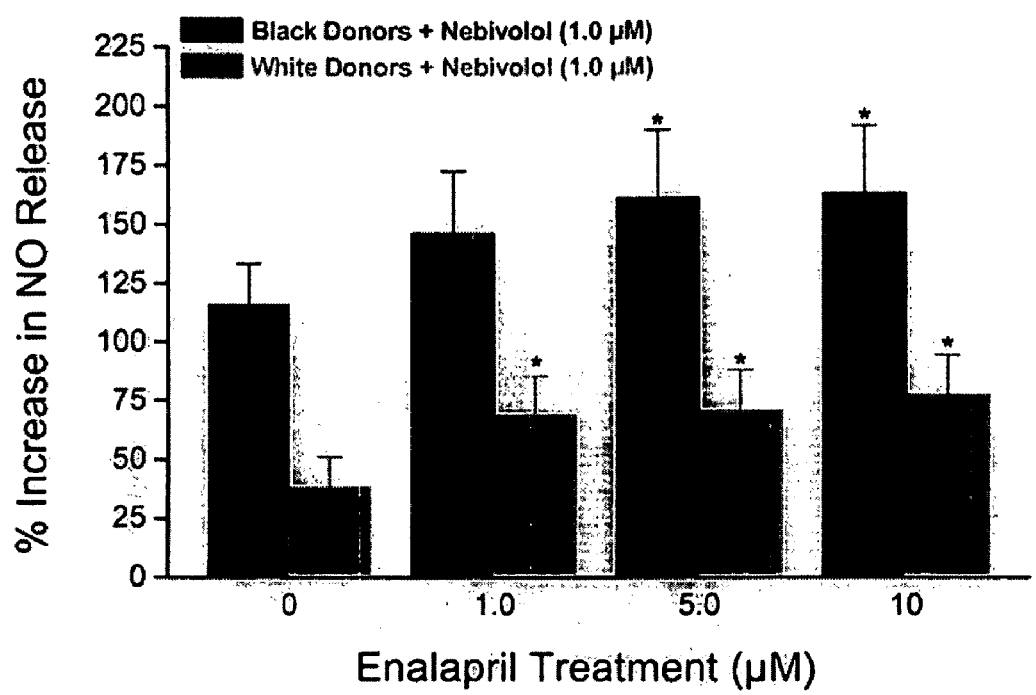
FIG. 4 depicts a comparison of the increase in NO release from Black and White donor endothelial cells after chronic treatment with enalapril followed by treatment with nebivolol (1 μM).

In FIG. 3, the extent of NO release from Black and White donors was measured with nebivolol (1 µM) following chronic treatment with the ACE-inhibitor, enalapril. As observed with ramiprilat (above), enalapril significantly enhanced the ability of nebivolol to increase NO release at concentrations of 5 and 10 µM and 1, 5 and 10 µM in Black and White donor cells, respectively. The magnitude of the increase is greater in endothelial cells from Blacks than Whites (FIG. 4).

There were significant concentration dependent effects on the ability of nebivolol to enhance NO release from Black and White donor endothelial cells that had been chronically treated with ACE inhibitors. Additionally, this property of the drug appears to work independently of β1-adrenoceptor blockade. By promoting a more normal vascular physiology through an NO-dependent pathway, nebivolol treatment may have better efficacy and fewer side effects as compared to agents that only inhibit the sympathetic nervous system. These data further support the hypothesis that nebivolol may have distinct pharmacologic benefits through modulation of endothelial function and NO metabolism.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein.

What is claimed is:

1. A composition comprising between about 0.125 mg to about 40 mg nebivolol or a pharmaceutically acceptable salt thereof and between about 1 mg to about 1200 mg of an angiotensin II receptor antagonist (ARB) selected from the group consisting of olmesartan, losartan, valsartan and pharmaceutically acceptable salts thereof wherein the composition provides a higher therapeutic index when administered to a patient having hypertension than either the corresponding amount of nebivolol or the ARB administered alone.

2. The composition of claim 1 wherein the ARB is olmesartan or a pharmaceutically acceptable salt thereof.

3. The composition of claim 1 wherein the ARB is losartan or a pharmaceutically acceptable salt thereof.

4. The composition of claim 1 wherein the ARB is valsartan or a pharmaceutically acceptable salt thereof.

5. A composition comprising between about 0.125 mg to about 40 mg nebivolol or a pharmaceutically acceptable salt thereof and between about 1 mg to about 1200 mg of an angiotensin II receptor antagonist (ARB) selected from the group consisting of olmesartan, losartan, valsartan and pharmaceutically acceptable salts thereof wherein the effectiveness of the composition when administered to a patient having hypertension is greater than the sum of the nebivolol or the ARB used alone.

6. The composition of claim 5 wherein the ARB is olmesartan or a pharmaceutically acceptable salt thereof.

7. The composition of claim 5 wherein the ARB is losartan or a pharmaceutically acceptable salt thereof.

8. The composition of claim 5 wherein the ARB is valsartan or a pharmaceutically acceptable salt thereof.

9. A composition comprising between about 0.125 mg to about 40 mg nebivolol or a pharmaceutically acceptable salt thereof and between about 1 mg to about 1200 mg of an angiotensin II receptor antagonist (ARB) selected from the group consisting of olmesartan, losartan, valsartan and pharmaceutically acceptable salts thereof wherein the composition is at least 100% more effective than treatment with nebivolol or the ARB administered alone.

10. The composition of claim 9 wherein the ARB is olmesartan or a pharmaceutically acceptable salt thereof.

11. The composition of claim 9 wherein the ARB is losartan or a pharmaceutically acceptable salt thereof.

12. The composition of claim 9 wherein the ARB is valsartan or a pharmaceutically acceptable salt thereof.

* * * * *